United States Patent
Fukuchi et al.

(10) Patent No.: US 6,710,031 B2
(45) Date of Patent: Mar. 23, 2004

(54) PROTEIN HAVING ANTITHROMBOTIC ACTIVITY AND METHOD FOR PRODUCING THE SAME

(75) Inventors: Naoyuki Fukuchi, Kawasaki (JP); Morikazu Kito, Kawasaki (JP); Takashi Kayahara, Kawasaki (JP); Fumie Futaki, Kawasaki (JP); Kohki Ishikawa, Kawasaki (JP); Eiichiro Suzuki, Kawasaki (JP); Keiko Gondoh, Kawasaki (JP); Nobuhisa Shimba, Kawasaki (JP); Naoyuki Yamada, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/969,763

(22) Filed: Oct. 4, 2001

(65) Prior Publication Data

US 2002/0198363 A1 Dec. 26, 2002

(30) Foreign Application Priority Data

Oct. 4, 2000 (JP) ......................................... 2000-305279

(51) Int. Cl.[7] ........................... A61K 38/46; C08H 1/00; C12Q 1/56
(52) U.S. Cl. ......................... 514/12; 530/350; 530/402; 435/13; 424/94.64
(58) Field of Search ................................ 530/350, 402, 530/412; 514/2, 822, 12; 424/94.64; 435/13

(56) References Cited

U.S. PATENT DOCUMENTS

| | | | | |
|---|---|---|---|---|
| 5,256,559 A | * | 10/1993 | Maraganore et al. | 435/240.2 |
| 5,744,584 A | * | 4/1998 | Scarborough et al. | 530/388.1 |
| 5,856,126 A | * | 1/1999 | Fukuchi et al. | 435/69.1 |
| 6,010,851 A | | 1/2000 | Mihara et al. | |
| 6,015,697 A | | 1/2000 | Mihara et al. | |
| 6,207,435 B1 | | 3/2001 | Mihara et al. | |

FOREIGN PATENT DOCUMENTS

EP 0 775 711 5/1997

OTHER PUBLICATIONS

Yee, D. (1998) "Introduction to protein folding—the process and factors involved" ProteinDesign, pp. 1–13.*
Fukuda, K. et al. (2000) Crystal structure of flavocetin–A, a platelet glycoprotein 1b–binding protein, reveals a novel cyclic tetramer of C–type lectin–like heterodimers. Biochemistry vol. 39, pp. 1915–1923.*
Zalipsky, S. et al. (1999) New detachable poly(ethylene glycol) conjugates: cysteine–cleavable lipopolymers regenerating natur phospholipid, diacyl phosphatidylethanolamine. Bioconjugate Chem. vol. 10, pp. 703–707.*
Bergeron, R. J. et al. (1997) Development of a Hypusine Reagent for Peptide Synthesis. J. Org. Chem. vol. 62, 3285–3290.*

* cited by examiner

*Primary Examiner*—Karen Cochrane Carlson
*Assistant Examiner*—Samuel W. Liu
(74) *Attorney, Agent, or Firm*—Oblon, Spivak, McClelland, Maier & Neustadt, P.C.

(57) ABSTRACT

A method for producing a protein having an antithrombotic activity, which comprises replacing, in a protein that has an amino acid sequence having a homology of not less than 30% to the amino acid sequence of SEQ ID NO: 1 and forms a higher order structure composed of a first β strand (β1), a first α helix (α1), a second α helix (α2), a second β strand (β2), a loop, a third β strand (β3), a fourth β strand (β4) and a fifth β strand (β5) in this order from the amino terminus, at least one amino acid residue in a region from α2 to β2 and/or a region from β3 to β4 so that electric charge of the amino acid residue is changed towards positive direction.

19 Claims, 9 Drawing Sheets

Figure 1:
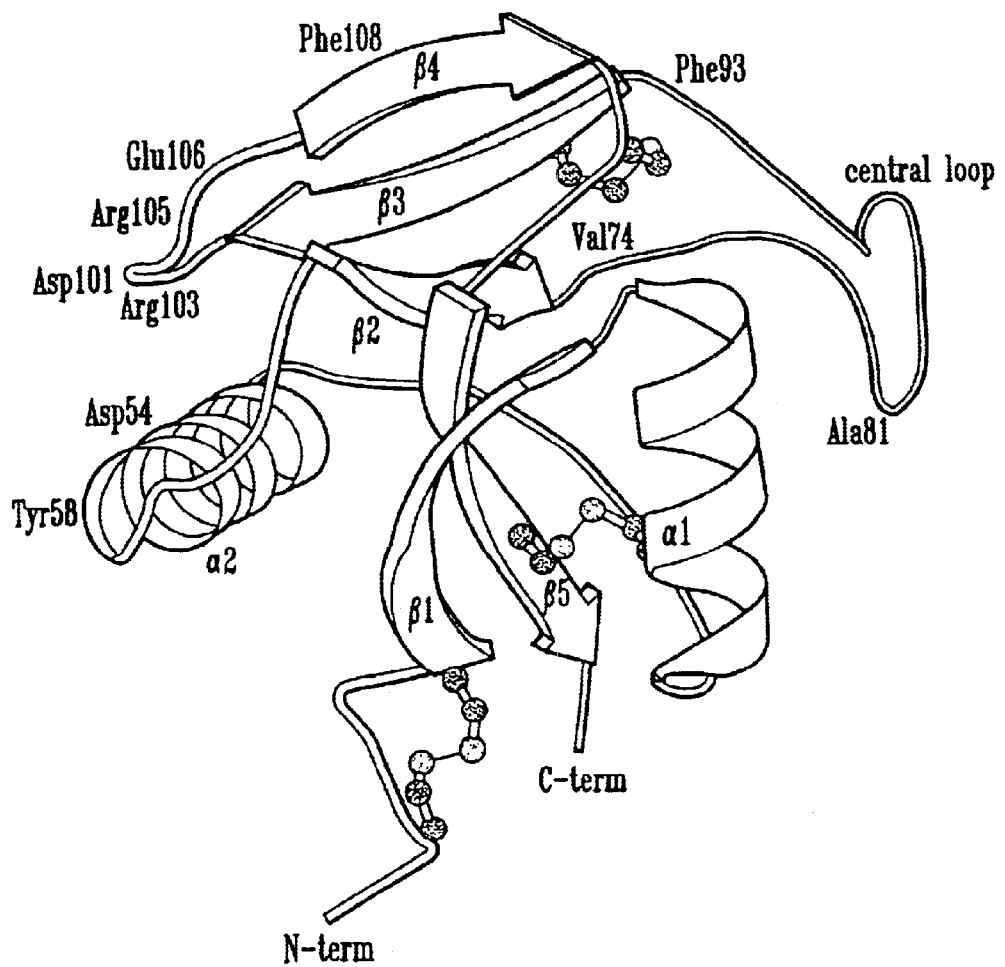

1 PFK
2 FTRPR
3 DLECPSGWSSYDRYCYK
  QEMTWADAERFCSEQAK
4 VDCEQQHSFICK
  EYLTRYIWIGLRECFMVSRDTRLREWFK
5 GGHLLSVETALEASFVDNVLYANK

```
                              SEQUENCE LISTING

<160> NUMBER OF SEQ ID NOS: 50

<210> SEQ ID NO 1
<211> LENGTH: 126
<212> TYPE: PRT
<213> ORGANISM: Crotallus horridus

<400> SEQUENCE: 1

Asp Leu Glu Cys Pro Ser Gly Trp Ser Ser Thr Asp Arg Tyr Cys Tyr
1               5                   10                  15

Lys Pro Phe Lys Gln Glu Met Thr Trp Ala Ser Ala Glu Arg Phe Cys
            20                  25                  30

Ser Glu Gln Ala Lys Gly Gly His Leu Leu Ser Val Glu Thr Ala Leu
        35                  40                  45

Glu Ala Ser Phe Val Asp Asn Val Leu Tyr Ala Asn Lys Glu Tyr Leu
    50                  55                  60

Thr Arg Tyr Ile Trp Ile Gly Leu Arg Val Gln Asn Lys Gly Gln Pro
65                  70                  75                  80

Cys Ser Ser Ile Ser Tyr Glu Asn Leu Val Asp Pro Phe Glu Cys Phe
                85                  90                  95

Met Val Ser Arg Asp Thr Arg Leu Arg Glu Trp Phe Lys Val Asp Cys
            100                 105                 110

Glu Gln Gln His Ser Phe Ile Cys Lys Phe Thr Arg Pro Arg
        115                 120                 125

<210> SEQ ID NO 2
<211> LENGTH: 690
<212> TYPE: DNA
<213> ORGANISM: Crotalus harridus
<220> FEATURE:
<221> NAME/KEY: CDS
<222> LOCATION: (66)..(512)
<223> OTHER INFORMATION:

<400> SEQUENCE: 2
ctgagcagac ttgctacctg tggaggccga ggaacagttc tctctgcagg gaaggaaaga      60 acgcc atg ggg cga ttc atc ttc gtg agc ttc aac ttg ctg gtc gtg ttc     110
      Met Gly Arg Phe Ile Phe Val Ser Phe Asn Leu Leu Val Val Phe
      1               5                   10                  15
```

```
ctc tcc cta agt gga act cta gct gat ttg gaa tgt ccc tcc ggt tgg      158
Leu Ser Leu Ser Gly Thr Leu Ala Asp Leu Glu Cys Pro Ser Gly Trp
            20                  25                  30 tct tcc tat gat cgg tat tgc tac aag ccc ttc aaa caa gag atg acc      206
Ser Ser Tyr Asp Arg Tyr Cys Tyr Lys Pro Phe Lys Gln Glu Met Thr
                35                  40                  45 tgg gcc gat gca gag agg ttc tgc tcg gag cag gcg aag ggc ggg cat      254
Trp Ala Asp Ala Glu Arg Phe Cys Ser Glu Gln Ala Lys Gly Gly His
        50                  55                  60 ctc ctc tct gtc gaa acc gcc cta gaa gca tcc ttt gtg gac aat gtg      302
Leu Leu Ser Val Glu Thr Ala Leu Glu Ala Ser Phe Val Asp Asn Val
    65                  70                  75 ctc tat gcg aac aaa gag tac ctc aca cgt tat atc tgg att gga ctg      350
Leu Tyr Ala Asn Lys Glu Tyr Leu Thr Arg Tyr Ile Trp Ile Gly Leu
80                  85                  90                  95 agg gtt caa aac aaa gga cag cca tgc tcc agc atc agt tat gag aac      398
Arg Val Gln Asn Lys Gly Gln Pro Cys Ser Ser Ile Ser Tyr Glu Asn
                100                 105                 110 ctg gtt gac cca ttt gaa tgt ttt atg gtg agc aga gac aca agg ctt      446
Leu Val Asp Pro Phe Glu Cys Phe Met Val Ser Arg Asp Thr Arg Leu
                115                 120                 125 cgt gag tgg ttt aaa gtt gac tgt gaa caa caa cat tct ttc ata tgc      494
Arg Glu Trp Phe Lys Val Asp Cys Glu Gln Gln His Ser Phe Ile Cys
        130                 135                 140 aag ttc acg cga cca cgt taagatccgg ctgtgtgaag tctggagaag              542
Lys Phe Thr Arg Pro Arg
            145 caaggaagcc ccccacctct ccccacccc caccttccgc aatctctgct cttccccctt     602 tgctcagtgg atgctctctg tagccggatc tgggttttct gctccagatg ggtcagaaga    662 tccaataaat tctgcctacc caaaaaaa                                       690

<210> SEQ ID NO 3
<211> LENGTH: 149
<212> TYPE: PRT
<213> ORGANISM: Crotalus harridus

<400> SEQUENCE: 3

Met Gly Arg Phe Ile Phe Val Ser Phe Asn Leu Leu Val Val Phe Leu
1               5                   10                  15

Ser Leu Ser Gly Thr Leu Ala Asp Leu Glu Cys Pro Ser Gly Trp Ser
            20                  25                  30

Ser Tyr Asp Arg Tyr Cys Tyr Lys Pro Phe Lys Gln Glu Met Thr Trp
        35                  40                  45

Ala Asp Ala Glu Arg Phe Cys Ser Glu Gln Ala Lys Gly Gly His Leu
    50                  55                  60

Leu Ser Val Glu Thr Ala Leu Glu Ala Ser Phe Val Asp Asn Val Leu
65                  70                  75                  80

Tyr Ala Asn Lys Glu Tyr Leu Thr Arg Tyr Ile Trp Ile Gly Leu Arg
                85                  90                  95

Val Gln Asn Lys Gly Gln Pro Cys Ser Ser Ile Ser Tyr Glu Asn Leu
            100                 105                 110

Val Asp Pro Phe Glu Cys Phe Met Val Ser Arg Asp Thr Arg Leu Arg
        115                 120                 125

Glu Trp Phe Lys Val Asp Cys Glu Gln Gln His Ser Phe Ile Cys Lys
    130                 135                 140

Phe Thr Arg Pro Arg
145
```

<210> SEQ ID NO 4
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
attggatcca tggatttgga atgtccctcc                                    30

<210> SEQ ID NO 5
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
ggacagccag cctccagcat cagtta                                        26

<210> SEQ ID NO 6
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
aataagctta acgtggtcgc gtgaacttgc                                    30

<210> SEQ ID NO 7
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
gatgctggag gctggctgtc ctttgt                                        26

<210> SEQ ID NO 8
<211> LENGTH: 54
<212> TYPE: DNA
<213> ORGANISM: ARTIFICIAL SEQUENCE
<220> FEATURE:
<223> OTHER INFORMATION: SYNTHETIC DNA

<400> SEQUENCE: 8
tatatctgga ttggactgag gggcggtgga ggtgaatgtt ttatggtgag caga         54

<210> SEQ ID NO 9
<211> LENGTH: 54
<212> TYPE: DNA
<213> ORGANISM: ARTIFICIAL SEQUENCE
<220> FEATURE:
<223> OTHER INFORMATION: SYNTHETIC DNA

<400> SEQUENCE: 9
tctgctcacc ataaacatt cacctccacc gccctcagt ccaatccaga tata           54

<210> SEQ ID NO 10
<211> LENGTH: 110
<212> TYPE: PRT
<213> ORGANISM: ARTIFICIAL SEQUENCE
<220> FEATURE:

<223> OTHER INFORMATION: SYNTHETIC PEPTIDE

<400> SEQUENCE: 10

```
Asp Leu Glu Cys Pro Ser Gly Trp Ser Ser Tyr Ser Arg Tyr Cys Tyr
1               5                   10                  15
Lys Pro Phe Lys Gln Glu Met Thr Tyr Ala Asp Ala Glu Arg Phe Cys
            20                  25                  30
Ser Glu Gln Ala Lys Gly Gly His Leu Leu Ser Val Glu Thr Ala Leu
        35                  40                  45
Glu Ala Ser Phe Val Asp Asn Val Leu Tyr Ala Asn Lys Glu Tyr Leu
    50                  55                  60
Thr Arg Tyr Ile Trp Ile Gly Leu Arg Phe Phe Phe Glu Cys Phe
65                  70                  75                  80
Met Val Ser Arg Asp Thr Arg Leu Arg Glu Trp Lys Val Asp Cys
                85                  90                  95
Glu Gln Gln His Ser Phe Ile Cys Lys Phe Thr Arg Pro Arg
                100                 105                 110
```

<210> SEQ ID NO 11
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 11
caagcccttc gcacaagaga tgac                                    24

<210> SEQ ID NO 12
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 12
gtcatctctt gtgcgaaggg cttg                                    24

<210> SEQ ID NO 13
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 13
gcatcctttg tggccaagtg gctc                                    24

<210> SEQ ID NO 14
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 14
gagcacattg gccacaaagg atgc                                    24

<210> SEQ ID NO 15
<211> LENGTH: 25
<212> TYPE: DNA
<213> ORGANISM: ARTIFICIAL SEQUENCE
<220> FEATURE:

<223> OTHER INFORMATION: SYNTHETIC DNA

<400> SEQUENCE: 15
gacaatgtgc tcgctgcgaa caaag        25

<210> SEQ ID NO 16
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 16
ctttgttcgc agcgagcaca ttgtc        25

<210> SEQ ID NO 17
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 17
ctatgcgaac gcagagtacc tcac        24

<210> SEQ ID NO 18
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 18
gtgaggtact ctgcgttcgc atag        24

<210> SEQ ID NO 19
<211> LENGTH: 23
<212> TYPE: DNA
<213> ORGANISM: ARTIFICIAL SEQUENCE
<220> FEATURE:
<223> OTHER INFORMATION: SYNTHETIC DNA

<400> SEQUENCE: 19
gcgaacaaag cgtacctcac acg        23

<210> SEQ ID NO 20
<211> LENGTH: 23
<212> TYPE: DNA
<213> ORGANISM: ARTIFICIAL SEQUENCE
<220> FEATURE:
<223> OTHER INFORMATION: SYNTHETIC DNA

<400> SEQUENCE: 20
cgtgtgaggt acgctttgtt cgc        23

<210> SEQ ID NO 21
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 21
gcgaacaaag aggccctcac acgt        24

```
<210> SEQ ID NO 22
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 22
acgtgtgagg gcctctttgt tcgc                                          24

<210> SEQ ID NO 23
<211> LENGTH: 22
<212> TYPE: DNA
<213> ORGANISM: ARTIFICIAL SEQUENCE
<220> FEATURE:
<223> OTHER INFORMATION: SYNTHETIC DNA

<400> SEQUENCE: 23
gtacctcaca gcttatatct gg                                            22

<210> SEQ ID NO 24
<211> LENGTH: 22
<212> TYPE: DNA
<213> ORGANISM: ARTIFICIAL SEQUENCE
<220> FEATURE:
<223> OTHER INFORMATION: SYNTHETIC DNA

<400> SEQUENCE: 24
ccagatataa gctgtgaggt ac                                            22

<210> SEQ ID NO 25
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 25
cctcacacgt gctatctgga ttgg                                          24

<210> SEQ ID NO 26
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 26
ccaatccaga tagcacgtgt gagg                                          24

<210> SEQ ID NO 27
<211> LENGTH: 22
<212> TYPE: DNA
<213> ORGANISM: ARTIFICIAL SEQUENCE
<220> FEATURE:
<223> OTHER INFORMATION: SYNTHETIC DNA

<400> SEQUENCE: 27
atggtgagcg cagacacaag gc                                            22

<210> SEQ ID NO 28
<211> LENGTH: 22
<212> TYPE: DNA
<213> ORGANISM: ARTIFICIAL SEQUENCE
<220> FEATURE:
<223> OTHER INFORMATION: SYNTHETIC DNA
```

-continued

```
<400> SEQUENCE: 28
gccttgtgtc tgcgctcacc at                                      22

<210> SEQ ID NO 29
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 29
ggtgagcaga gccacaaggc ttcg                                    24

<210> SEQ ID NO 30
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 30
cgaagccttg tggctctgct cacc                                    24

<210> SEQ ID NO 31
<211> LENGTH: 23
<212> TYPE: DNA
<213> ORGANISM: ARTIFICIAL SEQUENCE
<220> FEATURE:
<223> OTHER INFORMATION: SYNTHETIC DNA

<400> SEQUENCE: 31
agagacacag cgcttcgtga ggc                                     23

<210> SEQ ID NO 32
<211> LENGTH: 23
<212> TYPE: DNA
<213> ORGANISM: ARTIFICIAL SEQUENCE
<220> FEATURE:
<223> OTHER INFORMATION: SYNTHETIC DNA

<400> SEQUENCE: 32
ctcacgaagc gctgtgtctc tgc                                     23

<210> SEQ ID NO 33
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 33
gaacaaggct tgctgagtgg tttaaag                                 27

<210> SEQ ID NO 34
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 34
ctttaaacca ctcagcaagc cttgttc                                 27

<210> SEQ ID NO 35
<211> LENGTH: 27
```

```
<212> TYPE: DNA
<213> ORGANISM: ARTIFICIAL SEQUENCE
<220> FEATURE:
<223> OTHER INFORMATION: SYNTHETIC DNA

<400> SEQUENCE: 35
caaggcttcg tgcgtggttt aaagttg                                27

<210> SEQ ID NO 36
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 36
caactttaaa ccacgcacga agccttg                                27

<210> SEQ ID NO 37
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 37
cttcgtgagt gggctaaagt tgactg                                 26

<210> SEQ ID NO 38
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 38
cagtcaactt tagcccactc acgaag                                 26

<210> SEQ ID NO 39
<211> LENGTH: 41
<212> TYPE: DNA
<213> ORGANISM: ARTIFICIAL SEQUENCE
<220> FEATURE:
<223> OTHER INFORMATION: SYNTHETIC DNA

<400> SEQUENCE: 39
ggtgagcaga aacacaaggc ttcgtcagtg gtttaaagtt g                41

<210> SEQ ID NO 40
<211> LENGTH: 41
<212> TYPE: DNA
<213> ORGANISM: ARTIFICIAL SEQUENCE
<220> FEATURE:
<223> OTHER INFORMATION: SYNTHETIC DNA

<400> SEQUENCE: 40
caactttaaa ccactgacga agccttgtgt ttctgctcac c                41

<210> SEQ ID NO 41
<211> LENGTH: 41
<212> TYPE: DNA
<213> ORGANISM: ARTIFICIAL SEQUENCE
<220> FEATURE:
<223> OTHER INFORMATION: SYNTHETIC DNA

<400> SEQUENCE: 41
```

-continued ggtgagcaga gccacaaggc ttcgtgcgtg gtttaaagtt g         41

<210> SEQ ID NO 42
<211> LENGTH: 41
<212> TYPE: DNA
<213> ORGANISM: ARTIFICIAL SEQUENCE
<220> FEATURE:
<223> OTHER INFORMATION: SYNTHETIC DNA

<400> SEQUENCE: 42
caactttaaa ccacgcacga agccttgtgg ctctgctcac c         41

<210> SEQ ID NO 43
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 43
gcatcctttg tgaacaatgt gctc                            24

<210> SEQ ID NO 44
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 44
gagcacattg ttcacaaagg atgc                            24

<210> SEQ ID NO 45
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 45
caaggattcg tcagtggttt aaagttg                         27

<210> SEQ ID NO 46
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 46
caactttaaa ccactgacga agcctg                          27

<210> SEQ ID NO 47
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 47
ggattggact gaggtgcggt ggagg                           25

<210> SEQ ID NO 48
<211> LENGTH: 25
<212> TYPE: DNA
<213> ORGANISM: ARTIFICIAL SEQUENCE

-continued

```
<220> FEATURE:
<223> OTHER INFORMATION: SYNTHETIC DNA

<400> SEQUENCE: 48
cctccaccgc acctcagtcc aatcc                                          25

<210> SEQ ID NO 49
<211> LENGTH: 23
<212> TYPE: DNA
<213> ORGANISM: ARTIFICIAL SEQUENCE
<220> FEATURE:
<223> OTHER INFORMATION: SYNTHETIC DNA

<400> SEQUENCE: 49
ggacagccag catccagcat cag                                            23

<210> SEQ ID NO 50
<211> LENGTH: 23
<212> TYPE: DNA
<213> ORGANISM: ARTIFICIAL SEQUENCE
<220> FEATURE:
<223> OTHER INFORMATION: SYNTHETIC DNA

<400> SEQUENCE: 50
ctgatgctgg atgctggctg tcc                                            23
```

PROTEIN HAVING ANTITHROMBOTIC ACTIVITY AND METHOD FOR PRODUCING THE SAME

This patent application claims foreign priority benefits. Specifically, this patent application claims the benefit of the filing date under 35 U.S.C. 119 of Japanese Application No. 2000-305279, filed Oct. 4, 2000.

BACKGROUND OF THE INVENTION

The present invention relates to a protein having an antithrombotic activity and a method for producing the same. The present invention also relates to DNA coding for the protein and a drug containing the protein as an active ingredient.

The number of patients with thromboses such as myocardial infarction and cerebral thrombosis, in particular, arterial thrombosis, is high in the world, and these are very important diseases to be treated. In an early stage of onset of arterial thrombosis, von Willebrand factor in blood binds to subendothelial tissues (collagen etc.) exposed due to impairment of vascular endothelial cells, and a membrane glycoprotein on platelets, glycoprotein Ib, binds to the von Willebrand factor. Thus, the platelets adhere to blood vessel walls and they are activated (J. P. Cean et al., J. Lab. Clin. Med., 87, pp.586–596, 1976; K. J. Clemetson et al., Thromb. Haemost., 78, pp.266–270, 1997). Therefore, it is an important target for antithrombotic drugs for treating or preventing thromboses to inhibit the binding of von Willebrand factor and glycoprotein Ib. However, there are few substances that have proven to exhibit antithrombotic property by inhibiting the binding of these proteins, and such drugs have not been used in clinical practice. It has been reported that a recombinant protein VCL that has a sequence of the 504th to 728th amino acid residues of the amino acid sequence of von Willebrand factor shows an antithrombotic action by inhibiting the binding of von Willebrand factor and glycoprotein Ib (K. Azzam et al., Thromb. Haemost., 73, pp.318–323, 1995). Further, it has also been reported that a monoclonal antibody AJvW-2 directed to human von Willebrand factor exhibits an antithrombotic activity by specifically binding to von Willebrand factor without showing hemorrhagic tendency (S. Kageyama et al., Br. J. Pharmacol., 122, pp.165–171, 1997). It has also been shown that a monoclonal antibody 6B4 directed to glycoprotein Ib has an antithrombotic action in animal models (N. Cauwenberghs et al., Atherioscler. Thromb. Vasc. Biol., 20, pp.1347–1353, 2000). Furthermore, the protein AS1051 originating from snake venom specifically binds to platelet glycoprotein Ib to similarly exhibit antithrombotic property without showing hemorrhagic tendency (N. Fukuchi et al., WO95/08573).

Meanwhile, the binding of von Willebrand factor and glycoprotein Ib is not observed under a usual condition, but is considered to occur only under a condition where shear stress is induced, such as a condition in a blood flow (T. T. Vincent et al., Blood, 65, pp.823–831, 1985). However, as a method for artificially observing the binding of these proteins, there are known addition of an antibiotic, ristocetin (M. A. Howard and B. G. Firkin, Thromb. Haemost., 26, pp.362–369, 1971) and addition of a protein originating from snake venom, botrocetin (M. S. Read et al., Proc. Natl. Acad. Sci. USA., 75, pp.4514–4518, 1978). That is, both of the substances are considered to cause a structural change of von Willebrand factor by binding to a specific site of von Willebrand factor, thereby causing the binding of von Willebrand factor and glycoprotein Ib, which does not occur under a usual condition.

As proteins originating from snake venom, there are known, in addition to the aforementioned AS1051 (derivative of the α-chain of a protein originating from *Crotalus horridus horridus* snake venom, CHH-B) and its original protein, CHH-B, many glycoprotein Ib-binding proteins such as alboaggregin, echicetin, mamushigin, jararaca-GPIbBP and proteins originating from *Cerastes cerastes*. Many of these proteins have a heterodimeric structure, and the amino acid sequences of their subunits show a homology of not less than 30%. Furthermore, they are proteins in which all of subunits show an amino acid sequence homology of not less than 30% to the CHH-B α-chain (R. K. Andrews et al., Biochemistry, 35, pp.12629–12639, 1996; Y. Fujimura et al., Thromb. Haemost., 76, pp.633–639, 1996).

While such glycoprotein Ib-binding proteins originating from snake venom that inhibit the binding of glycoprotein Ib and von Willebrand factor and monoclonal antibodies directed to von Willebrand factor or glycoprotein Ib are known to exhibit an antithrombotic action as described above, some of proteins originating from snake venom that bind to a platelet membrane glycoprotein, glycoprotein IIb/IIIa, disintegrins (T. Matsui et al., Biochem. Biophys. Acta, 1477, pp.146–56, 2000) and monoclonal antibodies directed to glycoprotein IIb/IIIa (A. M. Lincoff et al., J. Am. Coll. Cardiol., 35, pp.1103–1115, 2000) have also been shown to exhibit an antithrombotic activity in animal experiments or clinical practice. For example, a peptide prepared from a disintegrin sequence, Eptifibatide (integrilin), has been shown to have clinical efficacy as an antithrombotic drug. Further, a chimerized monoclonal antibody directed to glycoprotein IIb/IIIa, Abciximab (ReoPro), is also widely used as an antithrombotic drug in clinical practice and its strong antithrombotic action and its therapeutic action for acute coronary syndromes have been reported (M. Madan et al., Circulation, 98, pp.2629–2635, 1998).

In addition to the above proteinaceous substances, low molecular weight organic compounds that bind to a platelet membrane glycoproteins and inhibit their function are known with respect to glycoprotein Ib (N. Fukuchi et al., WO99/54360; W. Mederski et al., WO00/32577; H. Matsuno et al., Circulation, 96, pp.1299–1304, 1997) and glycoprotein IIb/IIIa (E. J. Topol et al., Lancet, 353, pp.227–231, 1999). Among these, some of glycoprotein IIb/IIIa antagonists are clinically used, but they have not been shown to have efficacy as high as that of Abciximab (ReoPro) (E. J. Topol et al., Lancet, 353, pp.227–231, 1999; M. Madan et al., Circulation, 98, pp.2629–2635, 1998).

As described above, proteins that bind to platelet membrane proteins involved in thrombogenesis such as glycoprotein Ib and glycoprotein IIb/IIIa and inhibit their functions in thrombogenesis are useful as antithrombotic drugs, and many exogenous proteins have been developed as antithrombotic drugs. Among these, a chimerized monoclonal antibody directed to glycoprotein IIb/IIIa, Abciximab (ReoPro), shows high clinical efficacy. However, the following some conditions are still required to use proteinaceous substances, in particular, exogenous proteins as clinically usable drugs.

(1) High Binding Activity to Target

In the case of Abciximab (ReoPro), a high binding activity to platelets (glycoprotein IIb/IIIa) can be mentioned as one of the reasons for its high efficacy (R. M. Scarborough et al., Circulation, 100, pp.437–444, 1999). That is, it is considered that the administered Abciximab (ReoPro) firmly binds to platelets and as a result, it exists in blood together with platelets for a long period, thereby showing drug efficacy for a long period.

(2) Long Half-life/High Drug Efficacy Retention in Blood

For administration of a proteinaceous drug, in particular, a drug that is not originally an endogenous substance existing in the organisms, repetitive administration is generally difficult and a single administration is usually performed. Therefore, drug efficacy must be maintained for a certain long period and long half-life and/or high drug efficacy retention in blood is required.

(3) Low Antigenicity

Even when a single administration is performed, low antigenicity is required so that an excessive antigen-antibody reaction should not occur.

(4) Useful Actions in Addition to Main Action

There have been reported that Abciximab (ReoPro) actually has a binding action directed to other proteins such as αvβ3 integrin and Mac-1 in addition to an inhibitory action directed to glycoprotein IIb/IIIa (B. S. Coller, Thromb. Haemost., 82, pp.326–336, 1999). It is considered that this secondary action is one of the reasons for high clinical efficacy. That is, clinical efficacy of a drug may be increased by acting on several targets other than a single target.

It has been reported that a drug for inhibiting the binding of glycoprotein Ib and von Willebrand factor has a low risk of hemorrhage compared with a drug for inhibiting the function of glycoprotein IIb/IIIa (S. Kageyama et al., Br. J. Pharmacol., 122, pp.165–171, 1997), and therefore it can be a useful antithrombotic drug. Among the aforementioned proteins that inhibit the binding of glycoprotein Ib and von Willebrand factor, monoclonal antibodies generally have a high binding activity (affinity) to a target and can satisfy the above requirements (2) and (3) if they are modified into a chimera antibody or a humanized antibody. On the other hand, it is considered that proteins other than the monoclonal antibodies, for example, a glycoprotein Ib-binding protein originating from snake venom have a low binding activity (affinity) to their targets. For example, when the anti-platelet activity disclosed for a protein derivative originating from snake venom, AS1051 (N. Fukuchi et al., WO95/08573), is compared with that of a monoclonal antibody, AJvW-2 (S. Kageyama et al., Br. J. Pharmacol., 122, pp.165–171, 1997), the binding activity (affinity) of AS1051 on a molar concentration basis is calculated to be about 1/10 based on the fact that the efficacy is shown at almost the same concentration (weight concentration), and the molecular weight of AS1051 is about 15,000 Da and that of the monoclonal antibody about 150,000 Da.

Further, the present inventors found that, as shown in the examples described later, repetitive administration of AS1051 produces antibodies for AS1051 as an antigen and subsequent administration thereof caused platelet decrease that was considered to be attributable to the antibody generation.

That is, in order to clinically use glycoprotein Ib-binding proteins originating from snake venom such as AS1051 as antithrombotic drugs, they must further be improved for the aforementioned requirements (1) to (3).

SUMMARY OF THE INVENTION

The inventors of the present invention successfully elucidated a crystal structure of a glycoprotein Ib-binding protein originating from snake venom, AS1051, by preparing crystals of a specific mutant AS1051 and analyzing them by X-ray diffraction analysis, and thus identified a structure unique to AS1051. Moreover, they successfully improved glycoprotein Ib-binding proteins such as AS1051 by modifications based on the structure. That is, they found a method for improving a protein so that the protein should satisfy the aforementioned four kinds of properties, which were considered to be required to use an exogenous protein as a clinically applicable drug, i.e., (1) a high binding activity to target, (2) long half-life/drug efficacy retention in blood, (3) low antigenicity and (4) useful actions, in addition to its main action, as well as such an improved protein. Thus, they accomplished the present invention.

The present invention provides a method for producing a protein having an antithrombotic activity, which comprises replacing, in a protein that has an amino acid sequence having a homology of not less than 30% to the amino acid sequence of SEQ ID NO: 1 and forms a higher order structure composed of a first β strand (β1), a first α helix (α1), a second α helix (α2), a second β strand (β2), a loop, a third β strand (β3), a fourth β strand (β4) and a fifth β strand (β5) in this order from the amino terminus, at least one amino acid residue in a region from α2 to β2 and/or a region from β3 to β4 so that electric charge of the amino acid residue is changed towards positive direction (hereafter also referred to as the "production method of the present invention").

In the production method of the present invention, electric charge is preferably changed towards positive direction by replacing at least one acidic amino acid residue in the region from α2 to β2 and/or the region from β3 to β4 with a neutral amino acid residue.

In the production method of the present invention, the protein preferably originates from *Crotalus horridus horridus*.

Further, it is preferred that the region from α2 to β2 in the protein corresponds to the sequence of the amino acid numbers 47 to 72 in the amino acid sequence of SEQ ID NO: 1 and the region from β3 to β4 corresponds to the sequence of the amino acid numbers 94 to 111 in the amino acid sequence of SEQ ID NO: 1. In this embodiment, it is preferred that at least one acidic amino acid residue of which a carbon atom exists within 10 Å from the α carbon atom of the arginine residue of the amino acid number 103 in the amino acid sequence of SEQ ID NO: 1 is replaced with a neutral amino acid residue. Further, the acidic amino acid residue preferably is at least one residue selected from the aspartic acid residue of the amino acid number 54, the aspartic acid residue of the amino acid number 101 and the glutamic acid residue of the amino acid number 106 in the amino acid sequence of SEQ ID NO: 1.

The production method of the present invention may further comprise deleting a region containing the loop structure existing between β2 and β3 in such a manner that the higher order structures of β2 and β3 are maintained, or replacing the region with one or more amino acid residue(s) in a number required to maintain the higher order structures of β2 and β3, said amino acid residue(s) being selected from the group consisting of a glycine residue, an alanine residue, a serine residue and a cysteine residue. Preferably, the region containing the loop structure existing between β2 and β3 is replaced with an amino acid sequence composed of four glycine residues.

The production method of the present invention preferably further comprises bonding a polyoxyalkylpolyol group to the protein. Preferably, the protein contains a cysteine residue corresponding to a cysteine residue of the amino acid number 81 in the amino acid sequence of SEQ ID NO: 1, and the polyoxyalkylpolyol group is bonded to this cysteine residue. The polyoxyalkylpolyol group is preferably a polyethylene glycol group.

The present invention also provides a protein having an antithrombotic activity, which has an amino acid sequence showing a homology of not less than 30% to the amino acid sequence of SEQ ID NO: 1 and forms a higher order structure composed of a first β strand (β1), a first α helix (α1), a second α helix (α2), a second β strand (β2), a loop, a third β strand (β3), a fourth β strand (β4) and a fifth β strand (β5) in this order from the amino terminus, and wherein at least one amino acid residue in a region from α2 to β2 and/or a region from β3 to β4 is replaced so that electric charge of the amino acid residue in the regions is changed towards positive direction, said protein being the following (a) or (b) (hereafter also referred to as the "protein of the present invention"):

(a) a protein, in which the region from α2 to β2 has the sequence of the amino acid numbers 47 to 72 in the amino acid sequence of SEQ ID NO: 1 and the region from β3 to β4 has the sequence of the amino acid numbers 94 to 111 in the amino acid sequence of SEQ ID NO: 1;
(b) the protein according to (a), in which substitution, insertion or deletion of one or several amino acid residues is included in the region from α2 to β2 having the sequence of the amino acid numbers 47 to 72 in the amino acid sequence of SEQ ID NO: 1 and/or the region from β3 to β4 having the sequence of the amino acid numbers 94 to 111 in the amino acid sequence of SEQ ID NO: 1.

The protein of the present invention preferably comprises an amino acid sequence of the following (A) or (B):

(A) the amino acid sequence of the amino acid numbers 47 to 111 in the amino acid sequence of SEQ ID NO: 1;
(B) the amino acid sequence according to (A), in which the cysteine residue of the amino acid number 81 in the amino acid sequence of SEQ ID NO: 1 is replaced with an alanine residue.

The protein of the present invention may have the amino acid sequence in which a region containing the loop structure existing between β2 and β3 is deleted in such a manner that the higher order structures of β2 and β3 are maintained, or the region is replaced with one or more amino acid residue(s) in a number required to maintain the higher order structures of β2 and β3, said amino acid residue(s) being selected from the group consisting of a glycine residue, an alanine residue, a serine residue and a cysteine residue. The region preferably has the sequence in which the region containing the loop structure existing between β2 and β3 is replaced with an amino acid sequence composed of four glycine residues.

The protein of the present invention preferably has a sequence in which at least one acidic amino acid residue of which a carbon atom exists within 10 Å from the α carbon atom of the arginine residue of the amino acid number 103 in the amino acid sequence of SEQ ID NO: 1 is replaced with a neutral amino acid residue. In this embodiment, it is preferred that the acidic amino acid residue to be replaced is composed of at least one residue selected from the aspartic acid residue of the amino acid number 54, the aspartic acid of the amino acid number 101 and the glutamic acid residue of the amino acid number 106 in the amino acid sequence of SEQ ID NO: 1.

Preferably, the protein of the present invention is bonded to a polyoxyalkylpolyol group. The protein of this embodiment preferably contains a cysteine residue corresponding to the cysteine residue of the amino acid number 81 in the amino acid sequence of SEQ ID NO: 1, and the polyoxyalkylpolyol group is bonded to this cysteine residue. The polyoxyalkylpolyol group is preferably a polyethylene glycol group.

The present invention also provides a DNA coding for the protein of the present invention (hereafter also referred to as the "DNA of the present invention"), as well as a method for producing the protein of the present invention, which comprises steps of culturing a host microorganism transformed with the DNA of the present invention and collecting a protein encoded by the DNA from a culture and a method for producing the protein of the present invention, which comprises steps of culturing a host microorganism transformed with the DNA of the present invention, collecting a protein encoded by the DNA from a culture and bonding a polyoxyalkylpolyol group to the collected protein.

The present invention further provides a drug containing the protein of the present invention as an active ingredient. Also, the present invention provides a pharmaceutical composition comprising the protein of the present invention and a pharmaceutically acceptable carrier, and a use of the protein of the present invention for the manufacture of a medicament.

According to the present invention, a glycoprotein Ib-binding protein originating from snake venom can be improved to obtain a protein having (1) higher activity, (2) higher drug efficacy retention, (3) lower antigenicity, (4) thrombin-induced aggregation inhibitory action in addition to its main action, i.e., an inhibitory activity for binding of glycoprotein Ib and von Willebrand factor, and so forth, and the improved protein can be utilized as a more effective antithrombotic drug.

BRIEF EXPLANATION OF THE DRAWINGS

FIG. 1 shows a three-dimensional structure of AS1051 in a crystal.

FIG. 2 shows a reverse phase liquid chromatogram of AS1051-G4 after lysyl endopeptidase digestion and structures of its peptide chains.

FIG. 3 shows a reverse phase liquid chromatogram of polyethylene-glycolated AS1051 (AS1051-PEG5000) after lysyl endopeptidase digestion and structures of its peptide chains.

FIG. 4 shows inhibition curves of the polyethylene-glycolated AS1051 and mutant M23 proteins.

FIG. 5 shows inhibition for ristocetin-induced platelet aggregation by polyethylene-glycolated M23.

FIG. 6 shows inhibition for thrombin-induced platelet aggregation by the polyethylene-glycolated AS1051.

FIG. 7 shows numbers of platelets in guinea pigs after repetitive administrations of AS1051-Ala.

FIG. 8 shows results of detection of anti-AS1051-Ala antibodies in plasma of guinea pigs after repetitive administrations of AS1051-Ala.

FIG. 9 shows numbers of platelets in guinea pigs after repetitive administrations of AS1051-G4 and AS1051-PEG5000.

FIG. 10 shows ex vivo drug efficacy of M23-PEG20000, in which a) represents results of 5 minutes after the administration and b) represents results of 5 days after the administration.

DETAILED DESCRIPTION OF THE INVENTION

The present invention will be described in detail below. In the following description, an amino acid residue may be referred to by using a three-letter code. When a numeral is added to the three-letter code, the numeral represents an amino acid number in the amino acid sequence of SEQ ID NO: 1, unless otherwise specified. When a three-letter code is further added, it means replacement with an amino acid residue of the further added three-letter code (for example, "Cys81Ala" means that a cysteine residue of the amino acid number 81 in the amino acid sequence of SEQ ID NO: 1 is replaced with an alanine residue).

<1> Production Method of Present Invention and Protein of Present Invention

The production method of the present invention comprises replacing, in a protein that has an amino acid sequence having a homology of not less than 30% to the amino acid sequence of SEQ ID NO: 1 and forms a higher order structure composed of a first β strand (β1), a first α helix (α1), a second α helix (α2), a second β strand (β2), a loop, a third β strand (β3), a fourth β strand (β4) and a fifth β strand (β5) in this order from the amino terminus, at least one amino acid residue in a region from α2 to β2 and/or a region from β3 to β4 so that electric charge of the amino acid residue is changed towards positive direction.

The present invention was accomplished based on the following findings about the binding scheme of AS1051 to glycoprotein Ib on the basis of the crystal structure of AS1051 elucidated in the present invention.

Observation of the crystal structure of AS1051 revealed that a region forming two of α helices (α1 and α2) and a region forming five β strands (β1 to β5) were recognized from the N-terminus and that a region composed of β2, β3, β4 and α2 contained a large number of hydrophobic residues and basic residues exposed to a solvent. Therefore, single residue mutants in which hydrophobic residues, basic residues and acidic residues located in this region were replaced with Ala were prepared and their ability to bind to glycoprotein Ib was evaluated. The acidic residues were also replaced aiming at suppressing repulsion to a negatively charged region of Tyr276 to Glu282 in glycoprotein Ib by weakening the negative electric charge of AS1051 and enhancing affinity between them. The mutation was introduced into a protein so that a sequence between Val74 to Phe93 should be replaced with four Gly residues (AS1051-G4). The abilities of the prepared 14 mutants to bind to glycoprotein Ib are shown in Example 5 (Table 2). The mutant in which Tyr58, Lys61, Tyr67, Arg103, Arg105 or Phe108 was replaced with Ala showed a markedly decreased binding ability, while the mutant in which Asp54, Asp101 or Glu106 was replaced with Ala showed an increased binding ability.

Thus, it was revealed that the region containing these residues was a binding site for glycoprotein Ib. Further, it was suggested that the hydrophobic residues and the basic residues were involved in the binding to glycoprotein Ib and that the acidic residues repelled the negative electric charge of glycoprotein Ib.

Subsequently, six mutants shown in Example 6 (Table 3) were prepared since it was considered that the ability to bind to glycoprotein Ib could be further improved by simultaneously replacing Asp54, Asp101 and Glu106. To eliminate the negative electric charge of the acidic residues, replacement with Ala, Asn (in the case of Asp) or Gln (in the case of Glu) was used in combination. These replacements were used since improvement of the binding ability by single residue replacement with Ala was confirmed and Asn and Gln change only electric charge without changing the size. Among the prepared mutants, the Asp54Asn/Asp101Ala mutant showed a higher glycoprotein Ib-binding ability than that of the Asp101Ala mutant.

It is known that glycoprotein Ib is composed of an α-chain and a β-chain, and a domain binding to von Willebrand factor is in the N-terminus region of the α-chain (Titani et al., Proc. Nati. Acad. Sci. USA., 70, pp.538–542, 1987). This region is composed of 299 residues and is bonded with few saccharide chains. A region of His1 to Leu275 contains repeated sequences rich in Leu (leucine-rich repeats (Leu-rich repeats)) and has very high hydrophobicity. It has been reported that both of single residue replacements of Leu57 with Phe and Ala156 with Val in the Leu-rich repeats markedly decrease the binding of glycoprotein Ib to von Willebrand factor (Miller et aL, Blood, 79, pp.439–446, 1992; Ware et al., J. Clin. Invest., 92, pp.1213–1220, 1993). Further, a region of Tyr276 to Glu282 contains four acidic residues and three sulfated Tyr residues, and it has been reported that this region is involved in the binding to vWF (von Willebrand factor; Ward et al., Biochemistry, 35, pp.4929–4938, 1996). These reports support the above findings.

From the above, it is considered that, as for a protein that has antithrombotic activity similar to that of AS1051 and has such an amino acid sequence containing a region from α2 to β2 and a region from β3 to β4 in that order as in AS1051, its ability to bind to glycoprotein Ib can be improved by replacing an amino acid residue located in the region from α2 to β2 and/or the region from β3 to β4, which is considered to be important for the binding to glycoprotein Ib, with such an amino acid residue that changes electric charge towards positive direction.

Examples of the protein having antithrombotic activity similar to that of AS1051 include heterodimer proteins that bind to glycoprotein Ib originating from snake venom, for example, glycoprotein Ib-binding proteins originating from snake venom that have the same heterodimeric structure as that of CHH-B, wherein 30% or more of the amino acid sequences are homologous with that of the α-chain (AS1051) of CHH-B originating from Crotalus horridus horridus. In addition to the CHH-B α-chain, for example, it has been indicated that a glycoprotein Ib-binding activity is present in Echicetin (M. Peng et al., Biochem. Biophys. Res. Commun., 205, pp.68–72, 1994) and the β-chain of Jararaca-GPIb-BP (T. Kawasaki et al., J. Biol. Chem., 271, pp.10635–10639, 1996). The region from α2 to β2 and the region from β3 to β4 of these proteins can also be identified by alignment of amino acid sequences or alignment of the three-dimensional structures (threading). Further, subunits having a glycoprotein Ib-binding activity of other heterodimer glycoprotein Ib-binding proteins originating from snake venom are likewise applicable. A position of a subject structure for designing an improved protein in a subunit of a protein of interest can be identified by using a method such as X-ray crystallography or NMR of the protein. However, as shown in the present specification, it can also be attained by estimating a subject partial structure in AS1051, a partial structure existing at positions corresponding to amino acid residues, or the amino acid residues through alignment of amino acid sequence with the three-dimensional structure of AS1051 or alignment of the three-dimensional structures (threading). The alignment of amino acid sequences can be performed by using a program of BLAST or the like. As for BLAST, a file compatible with a computer to be used can be obtained from files existing in ncbi.nlm.nih.gov/blast/ excutable by using FTP. Further, the threading can also be performed by using a program of INSIGHT II, COMPASS or the like. INSIGHT II and COMPASS are commercially available from MSI and Protein Engineering Research Institute, respectively.

In the mutant AS1051, all the residues of which replacement with Ala markedly decrease the activity, that is, amino acid residues that are considered to be important for binding to glycoprotein Ib, Tyr58, Lys61, Tyr67, Arg103, Arg105 and Phe108, exist in the region from α2 to β2 (Ala47 to Leu72) and the region from β3 to β4 (Glu94 to Asp111) judging from their crystal structures. When the above alignment (threading) method is applied to, for example, the β-chain of echicetin, which has been reported to bind to glycoprotein Ib (M. Peng et al., Biochem. Biophys. Res. Commun., 205, pp.68–72, 1993; EMBL/GenBank accession number: P81996), the result of BLAST shows that sequences corresponding to a sequence considered to be the binding region of the above AS1051 to glycoprotein Ib exist between Ser45 and Leu68 and between His95 and Lys110, while the result of COMPASS shows that they exist between Ser45 and Asp70 and between Glu93 and Lys110. Since eight basic amino acid residues (Arg43, Lys46, Lys60, Arg94, Lys100, Arg108, Arg109, Lys110) exist in this region, these results support that this region corresponds to the region in AS1051 that is important for the binding to glycoprotein Ib. Therefore, as in the case of AS1051, the present invention also includes a method of increasing the activity by changing electric charge of an amino acid residue having an α carbon atom within 10 Å from the α carbon in these basic amino acids towards positive direction. Since acidic amino acid residues (Glu47, Asp49, Glu62, Asp70, Glu93, Asp103) exist in this region, it is considered to be preferable to replace at least one of these amino acid residues with a neutral amino acid residue. Further, a similar method is applicable to other glycoprotein Ib-binding proteins originating from snake venom, which are homologous to AS1051.

Proteins having antithrombotic activity similar to that of AS1051 contain an amino acid sequence having a homology of, usually not less than 20%, preferably not less than 30%, to the amino acid sequence of SEQ ID NO: 1. Therefore, a protein to be modified can be easily selected in this range. The values of homology to the amino acid sequence of SEQ ID NO: 1 are those calculated by the aforementioned method using BLAST.

Regions forming α helixes and β strands can be identified by using an estimation method known to those skilled in the art.

Replacement with an amino acid residue that can change electric charge towards positive direction include replacement of an acidic amino acid residue with a neutral or basic amino acid residue and replacement of a neutral amino acid residue with a basic amino acid residue. Preferred is replacement of an acidic amino acid residue with a neutral amino acid residue. A plurality of amino acid residues may be replaced.

Examples of the acidic amino acid residue include Asp, Glu and so forth. Examples of the neutral amino acid residue include Gly, Ser, Thr, Cys, Tyr, Asn, Gln, Ala, Val, Leu, Ile, Met, Trp, Phe, Pro and so forth. Examples of the basic amino acid residue include Arg, His, Lys and so forth.

Specific examples of the proteins having antithrombotic activity similar to that of AS1051 include those containing an amino acid sequence of the following (A) or (B):

(A) an amino acid sequence of the amino acid numbers 47 to 111 in the amino acid sequence of SEQ ID NO: 1;
(B) the amino acid sequence according to (A), in which Cys of the amino acid number 81 in the amino acid sequence of SEQ ID NO: 1 is replaced with Ala.

In those proteins, the region from α2 to β2 is a region corresponding to the amino acid numbers 47 to 72 in the amino acid sequence of SEQ ID NO: 1 and the region from β3 to β4 is a region corresponding to the amino acid numbers 94 to 111 in the amino acid sequence of SEQ ID NO: 1. In these proteins, an acidic amino acid residue having an α carbon atom within 10 Å from the α carbon atom in Arg of the amino acid number 103 in the amino acid sequence of SEQ ID NO: 1 is preferably replaced with a neutral amino acid residue. Alternatively, it is preferred that an acidic amino acid residue within amino acid numbers 47 to 59 and 100 to 106 in the amino acid sequence of SEQ ID NO: 1 is replaced with a neutral amino acid residue. Further, it is more preferred that the acidic amino acid residue is composed of one or more of residues selected from Asp of the amino acid number 54, Asp of the amino acid number 101 and Glu of the amino acid number 106 in the amino acid sequence of SEQ ID NO: 1. The distance between αcarbons is determined by X-ray crystallography of the protein.

The production method of the present invention may comprise removal of the loop structure region that is not involved in the glycoprotein Ib-binding activity. That is, a region containing the loop structure existing between β2 and β3 may be deleted in such a manner that the higher order structures of β2 and β3 are maintained, or replaced with one or more amino acid residue(s) required to maintain the higher order structures of β2 and β3, which amino acid residue(s) are selected from the group consisting of Gly, Ala, Ser and Cys. It is preferred that a region containing the loop structure is replaced with an amino acid sequence composed of four Gly residues.

This embodiment of the present invention was accomplished based on the following findings about the crystal structure of AS1051 elucidated in the present invention.

Based on the crystal structure, it was revealed that a region in the vicinity of Cys81 (crystal was prepared as for the protein containing the mutation of Cys81Ala) involved in formation of dimer of AS1051, which originally exists as a heterodimer, had a flexible loop structure with high hydrophobicity. In the heterodimer protein existing in snake venom, CHH-B, the AS1051 moiety, i.e., the α-chain, binds to the β-chain via Cys81. In consideration that the loop structure found in the present invention was important for this dimer formation and was not involved in the binding to glycoprotein Ib, a protein in which a sequence from Val74 to Phe93 was replaced with four Gly residues (AS1051-G4) was designed in order to remove the region containing the loop structure without changing the whole structure of the protein.

It was elucidated by preparing a protein AS1051-G4 and determining its inhibitory activity for binding of AS1051 to glycoprotein Ib and von Willebrand factor that the region containing the flexible loop structure from Val74 to Phe93 was important for the dimer formation, but was not involved in the binding to glycoprotein Ib. That is, the prepared AS1051-G4 exhibited almost the same inhibitory activity as that of AS1051. It was considered that such a loop structure with high hydrophobicity was easily recognized as an antigen (immunodominant), deteriorated stability of the protein in a solution and so forth. As a result of repetitive administrations of AS1051-G4 to animals in the same manner as performed with AS1051, it was suggested that its platelet-reducing action was weaker and hence it had decreased antigenicity. Further, a protein in which a peptide chain having a binding activity is maintained and a region not involved in the activity is replaced with Gly to decrease antigenicity is also obtained in, for example, transformation of a protein originating leech saliva, hirudin, to hirulog (G. F. Pineo and R. D. Hull, Curr. Opin. Hematol., 2, pp.380–5, 1995). Therefore, the finding of a partial structure not involved in such an activity in a subunit of a glycoprotein Ib-binding protein originating from snake venom and the finding that this partial structure can be replaced with a Gly chain are considered to be applicable to other glycoprotein Ib-binding proteins originating from snake venom having a homologous amino acid sequence.

In AS1051, for example, the region containing the loop structure between β2 and β3 corresponds to a sequence from Val74 to Phe93, and the number of residues required to maintain the higher order structure of β2 and β3 is four residues. However, the starting position and the end position of the partial sequence to be removed may be moved backward or forward about 10 residues, preferably about 3 to 5 residues. Further, the length of Gly chain to be inserted instead can be a length that provides the most desired activity in the range of 0 to 10 residues. Further, instead of Gly, amino acid residues showing low hydrophobicity such as Ala, Ser and Cys may also be used.

Specific examples of the protein in which a region containing the loop structure is removed include a protein in which a sequence from Val74 to Phe93 in AS1051 is replaced with four Gly residues (AS1051-G4) and a protein in which Met corresponding to the translation initiation point is added to its amino terminus.

The loop structure region not involved in the glycoprotein Ib-binding activity in proteins other than AS1051 and the required number of residues can be identified based on comparison of their amino acid sequences with that of AS1051.

According to this embodiment of the present invention, a protein that maintains an inhibitory activity for binding of glycoprotein Ib and von Willebrand factor (glycoprotein Ib/von Willebrand factor binding inhibitory activity) and has decreased antigenicity can be obtained.

Further, the improved proteins obtained as described above are preferably modified with polyoxyalkylpolyol to attain (1) increased half-life/drug efficacy retention in blood and (2) decreased antigenicity. This embodiment of the present invention was accomplished based on the following findings.

It was observed that polyethylene-glycolation of an improved protein of AS1051 decreased or eliminated antigenicity observed upon the administration of AS1051 to animals, and inhibited thrombin-induced platelet aggregation, which was not observed with AS1051. The thrombin-induced aggregation inhibitory activity has been reported for some glycoprotein Ib-binding proteins originating from snake venom, but has not been recognized in AS1051 or CHH-B. Therefore, it is considered that their binding positions on glycoprotein Ib are different from those of the reported proteins (M. C. Chang et al., Blood, 91, pp.1582–9, 1998). The glycoprotein Ib is considered to be one of platelet receptors to thrombin (G. A. Jamieson, Thromb. Haemost., 78, pp.242–246, 1997), and it is also considered that inhibition of thrombin-induced platelet aggregation without affecting thrombin-induced coagulation reaction is an effective target of an antithrombotic drug (P. Andrew-Gordon et al., Proc. Natl. Acad. Sci. USA., 96, pp.12257–12262, 1999). It is considered that the inhibitory activity on thrombin-induced aggregation provided by the polyethylene-glycolation according to the present invention, not because the binding site on glycoprotein Ib was changed, but because steric hindrance by the polyethylene glycol region affected the binding of thrombin and glycoprotein Ib.

Further, when a polyethylene-glycolated mutant having an increased activity was administered in a dose 10 times as much as the minimal drug efficacy concentration, retention of the inhibitory activity on platelet aggregation (botrocetin-induced aggregation) dependent on glycoprotein Ib and von Willebrand factor, which is the drug efficacy, was observed even 5 days (120 hours) after the administration.

Specific examples of polyoxyalkylpolyol include polyethylene glycol and so forth. Specific examples of its binding position include an amino group, a carboxyl group, a thiol group and so forth.

In this embodiment, it is preferred that the protein contains Cys corresponding to Cys of the amino acid number 81 in the amino acid sequence of SEQ ID NO: 1 and a polyoxyalkylpolyol group is bonded to this Cys. Further, in the case of a protein where the region containing the loop structure between β2 and β3 is replaced, if Cys is contained in the amino acid residue with which the loop structure is replaced, the polyoxyalkylpolyol group may be bonded to the Cys.

Polyoxyalkylpolyolation is performed by, for example, the following steps (a) and (b).

(1) Step (a)

First, a protein or an oligomer thereof is denatured by using a protein-denaturing agent in a solution. Then, the denaturing agent is removed from the solution in the presence of polyoxyalkyl polyether having a functional group that reacts with a thiol group to refold a subunit peptide.

A solvent of the solution is usually water. The protein-denaturing agent is not particularly limited so long as it can reversibly denature a protein. Examples thereof include guanidine hydrochloride, urea and so forth. The protein-denaturing agent can be used at any concentration so long as the protein is dissolved. However, for example, it can be used in the range of from 1 M to a saturated concentration, preferably, from 2 M to 8 M. pH of the solution is not limited, but it is preferably in the range of from 7 to 12, in which cleavage of a disulfide bond and binding of polyethylene glycol to a thiol group, which will be explained later, readily occur. The temperature of the solution is not also particularly limited, but it is preferably in the range from 0 to 40° C. The reaction time is also appropriately selected. The denaturation may be performed under either reducing conditions or non-reducing conditions.

A disulfide bond in a protein or an oligomer thereof may be cleaved beforehand by using a reducing agent, but this is not essential. A substance containing Cys such as glutathione, a reducing agent such as dithiothreitol, an enzyme such as a protein disulfide isomerase or the like can be added before the refolding process.

When a protein or an oligomer thereof has a disulfide bond between proteins or a disulfide bond within the protein which is different from the disulfide bond in the original protein, the denaturation is preferably performed under reducing conditions. In the present invention, the reducing conditions means conditions under which cleavage of a disulfide bond is promoted as in the presence of a substance containing Cys, a reducing agent, protein disulfide isomerase or the like. Since cleavage of the disulfide bond is promoted under reducing conditions, the reaction with polyoxyalkyl polyether having a functional group that reacts with a thiol group is promoted in the refolding process. When an oligomer is denatured, it is particularly preferred that the denaturation is performed under reducing conditions because cleavage of a disulfide bond between proteins is promoted.

Subsequently, the denaturing agent is removed from the solution containing the denatured protein in the presence of polyoxyalkyl polyether having a functional group that reacts with a thiol group. The denaturing agent can be removed from the solution by, for example, dialysis.

Typical examples of the functional group that reacts with a thiol group include a maleimide group (R. J. Goodson et al., Bio/Technology, 8, p.343, 1990), orthopyridyl disulfide group (M. Yokoyama et al., Biochem. Biophys. Res. Commun., 164, p.1234, 1989), vinylsulfone group (Shearwater Polymers Inc. Item No. M-VS-5000) and so forth. The functional group is not limited so long as it preferentially bonds to a thiol group. Examples of the polyoxyalkyl polyether include polyethylene glycol, polypropylene glycol, polyhydroxyethyl glycerol, dextran, carbohydrate polymers and so forth. The molecular weight is not particularly limited, but it is preferably in the range of from 1000 to 1,000,000, more preferably in the range of from 2000 to 50,000, in view of improvement of solubility and decrease of antigenicity of a protein to be obtained, and reactivity with a protein.

The polyoxyalkyl polyether described above may be added to the solution before or after denaturation of a protein or an oligomer thereof. It may also be added before removing the denaturing agent. Usually, it is preferred that after a protein or an oligomer thereof is denatured with a denaturing agent, the polyoxyalkyl polyether is added and the mixture is allowed to react for a certain period of time and then the denaturing agent is removed from the solution. The amount of polyoxyalkyl polyether is preferably an equimolar amount or more to the amount of the protein to be reacted.

The polyoxyalkyl polyether bonds to Cys of a protein by allowing the protein to react with polyoxyalkyl polyether having a functional group that reacts with a thiol group during or after the denaturation.

When the denaturing agent is removed from the solution as described above, refolding of the denatured protein occurs, and thus a peptide having a physiological activity identical to the physiological activity of the protein before modification or an activity of inhibiting the physiological activity can be obtained.

By performing natural oxidation (air oxidation) to form a disulfide bond within a protein and then adding polyoxyalkyl polyether having a functional group that reacts with a thiol group before the step of removing the denaturing agent from the solution containing the denatured protein, a polyoxyalkyl polyether group can be selectively and efficiently bonded to Cys originally involved in formation of a disulfide bond between subunits of the oligomeric protein.

(2) Step (b)

The protein bonded to polyoxyalkyl polyether, which is produced as described above, is isolated from the solution. This operation can be performed by a combination of operations used for conventional purification of a protein, that is, widely used chromatography techniques such as ion exchange, gel filtration or reverse phase chromatography, electrophoresis, precipitation operation such as salting out, desalting operation, concentration operation and so forth.

An aimed protein and polyoxyalkyl polyether can be separated by the above operations. When an oligomeric protein is used as a start material, the aimed protein and other proteins can be separated. For example, a protein having decreased antigenicity in which polyoxyalkyl polyether is bonded to Cys originally involved in formation of a disulfide bond between proteins in an oligomeric protein among Cys in the protein can be separated from the other proteins.

The binding position of polyoxyalkyl polyether bonded to a protein is preferably at Cys that forms a disulfide bond between proteins in the oligomeric protein. However, when the formation of the disulfide bonds is not determined, it may be such a position that the polyoxyalkyl polyether bonds to a specific thiol group, whereby the protein has an aimed activity, stably exists in a solution and preferably has decreased antigenicity. The other disulfide bonds within the protein are preferably the disulfide bonds within the protein of the original oligomer. However, they can be different from them in such a degree that the protein still has a substantial physiological activity. Further, when the original disulfide bond within the protein is not determined, it may be such a position that the protein is identifiable as a single molecule having a physiological activity and stably exists in a solution. The number of polyoxyalkyl polyether molecules to be bonded per molecule is preferably equal to the number of Cys forming a disulfide bond between proteins in the original dimer protein. However, when the number is not determined, it may be such a number that the obtained polyoxyalkyl-polyetherated monomer protein has a physiological activity, be identifiable as a single molecule and stably exists in a solution.

In the present invention, the modification with polyethylene glycol not only decreases antigenicity upon administration to animals, but also increases the glycoprotein Ib/von Willebrand factor binding inhibitory activity. That is, by modifying a protein in which its activity is increased through such replacement that electric charge of amino acid residues in a specific region should be changed towards positive direction according to the present invention, an improved protein can be finally obtained by polyethylene-glycolation, which has (1) a markedly increased glycoprotein Ib/von Willebrand factor binding inhibitory activity compared with a protein before the improvement and (2) extremely prolonged retention of drug efficacy (glycoprotein Ib/von Willebrand factor inhibiting inhibitory activity) after administration to animals.

A protein prepared by a combination of (1) such replacement that electric charge of amino acid residues in the aforementioned specific region should be changed towards positive direction, (2) removal of the loop structure region not involved in the glycoprotein Ib-binding activity and (3) polyoxyalkylpolyolation maintains high drug efficacy (inhibitory effect on glycoprotein Ib/von Willebrand factor binding) even 5 days after the administration to animals and has a novel activity that is not observed in the original protein, i.e., thrombin-induced platelet aggregation inhibitory action, and the antigenicity observed in the original protein is removed.

The protein of the present invention is a protein that can be produced by the production method of the present invention.

In the case of AS1051, a residue of the amino acid number 81 in the amino acid sequence of SEQ ID NO: 1 may be Ala or Cys in a protein before modification. Further, Met corresponding to the translation initiation point may be added to an amino terminus. Further, an improved AS1051 prepared by the aforementioned "removal of the loop structure region not involved in the glycoprotein Ib-binding activity" can also be used.

The residues most desired for the amino acid replacement in the amino acid sequence of SEQ ID NO: 1 are Asp101, Glu106 and Asp54. These mutations may be such replacements with an amino acid that electric charge should be changed. However, Asp is preferably replaced with Ala, Ser or Asn, and Glu is preferably replaced with Ala, Ser or Gln so that the whole structure of the protein should not be greatly changed. Further, as for the number of the amino acids to be replaced, one of the aforementioned amino acids may be replaced or a plurality of them may be replaced in combination.

More specifically, examples of the protein of the present invention include AS1051 having the amino acid sequence of SEQ ID NO: 1, such a protein in which its Cys81 is replaced with Ala and a protein wherein a part of the amino acid sequence is removed as in the above example, for example, the aforementioned AS1051-G4, in which one or more amino acid residues of Asp54, Asp101 and Glu106 (numerals are amino acid numbers corresponding to those in SEQ ID NO: 1 and, in a protein obtained by modifying a part of SEQ ID NO: 1, numerals are amino acid numbers parallerized in consideration to the change of an amino acid number) are replaced, i.e., Asp is replaced with one of amino acids having different characteristics such as Ala, Ser and Asn, and Glu is replaced with one of amino acids having different characteristics such as Ala, Ser and Gln.

The scheme of the disulfide bonds in the molecule of the protein of the present invention is preferably the same as that of the original dimeric protein, CHH-B. However, since the scheme in a natural-type CHH-B has not been reported, it may be the same as, for example, that of AS1051 having substantial physiological activity (N. Fukuchi et al., WO95/08573) or it may be different in such a degree that the physiological activity is not greatly lost. Further, when the disulfide bond in the original subunit is not determined, it is not particularly limited so long as it can be identified as a single molecule having a physiological activity and stably exists in a solution. Further, the amino acid sequences may include insertion, deletion, substitution and so forth in a part of amino acid residues so long as they do not substantially change the antithrombotic activity.

Further, properties of the protein obtained by the production method of the present invention are not particularly limited so long as they include one or a combination of (1) an increased binding activity to a target (glycoprotein Ib), (2) increased half-life/drug efficacy retention in blood, and (3) decreased antigenicity compared with a protein before the improvement. The increased binding activity specifically means that the Kd value for glycoprotein Ib becomes ½ or less or the $IC_{50}$ value of glycoprotein Ib/von Willebrand factor binding inhibitory activity becomes ½ or less compared with those of a protein before the improvement under the same measurement conditions. Further, the increased half-life/drug efficacy retention in blood is not particularly limited so long as a significant increase of the half-life/drug efficacy retention in blood is observed compared with a protein before the improvement. Where there are obtained no findings about the half-life/drug efficacy retention in blood of the protein before the improvement, it is sufficient that drug efficacy retention of 1 day (24 hours) or longer after administration should be observed in consideration of general characteristics of an exogenous protein. Further, it is sufficient that the antigenicity should be substantially decreased compared with a protein before the improvement. Where there are obtained no findings about antigenicity of the protein before the improvement, it may be such antigenicity that biological and biochemical reactions attributable to an antigen-antibody reaction should not occur when the obtained improved protein is administered to an animal in a minimal dose required to provide the obtained drug efficacy and in a minimal number of times required for immunization and then administered again.

Examples of the physiological activity of the protein obtained by the production method of the present invention include an inhibitory action for glycoprotein Ib-dependent platelet aggregation (platelet aggregation attributable to an inducing substance such as ristocetin or botrocetin) exerted by binding to glycoprotein Ib, antithrombotic action, anti-inflammatory action and analgesic action based on platelet adhesion inhibition and so forth.

The antithrombotic activity can be evaluated by a known method, for example, a method for determining an inhibitory activity for binding of glycoprotein Ib and von Willebrand factor, which will be described in the examples later.

Replacement of an amino acid in the production method of the present invention can be performed by preparing a DNA coding for an amino acid sequence after replacement as described in the explanation about the DNA of the present invention mentioned later. A modified protein in which an amino acid is replaced can be prepared by culturing a host microorganism transformed with that DNA and collecting a protein encoded by the DNA from a culture.

<2> DNA of Present Invention and Method for Producing Protein of Present Invention Using the Same The DNA of the present invention is a DNA coding for the protein of the present invention. The protein of the present invention can be prepared by culturing a host microorganism transformed with the DNA of the present invention and collecting a protein encoded by the DNA from a culture. Further, the polyoxyalkylpolyolated protein of the present invention can be produced by bonding a polyoxyalkylpolyol group to the collected protein.

The DNA of the present invention can be prepared by obtaining DNA coding for a protein before modification (target protein) and modifying this DNA.

When the amino acid sequence of the protein or the full length or a part of the nucleotide sequence of DNA coding for the protein is known, the DNA coding for the target protein can be obtained by the polymerase chain reaction (PCR) method using primers prepared based on a known nucleotide sequence. Alternatively, it can also be obtained from a cDNA library by performing hybridization using a probe prepared based on a known nucleotide sequence. Further, when DNA coding for the target protein is deposited at a depository, the deposited DNA can be used. Further, the whole nucleotide sequence of the gene is known, the DNA can be chemically synthesized. For example, the *E. coli* HB101/pCHA1 (*E. coli* AJ13023) strain harboring a plasmid containing the gene sequence of AS1051 was deposited at the National Institute of Bioscience and Human-Technology, Agency of Industrial Science and Technology, Ministry of International Trade and Industry (postal code: 305-8566, 1–3, Higashi 1-chome, Tsukuba-shi, Ibaraki-ken, Japan) as an international deposition under the provisions of the Budapest Treaty on Aug. 12, 1994, and received an accession number of FERM BP-4781.

DNA coding for the improved protein (mutant protein gene) can also be obtained by the PCR method using DNA coding for the target protein obtained as described above as a template and primers prepared so as to include a mutated nucleotide sequence, or by cleaving the gene and replacing it with a nucleotide sequence containing a mutation.

An expression system of the mutant protein gene obtained as described above using a microorganism can be constructed by incorporating the gene coding for the protein into a protein expression vector having a promoter that can be expressed in a commercially available host or a host prepared by using, for example, *Escherichia coli, Bacillus subtilis*, yeast or the like, and the gene can be expressed. The protein to be expressed can be directly expressed in the form having a signal sequence or in the form of a protein encoded by the gene coding for the protein, to which a translation initiation codon, methionine is added. It can also be expressed as a fusion protein to which a maltose binding protein (MBP), glutathione S-transferase (GST), calmodulin binding peptide, thioredoxin, His-tag or the like is added. Examples of the vector for the former direct expression include vectors such as pET (stratagene), pGEMEX (Promega), pTrc99A (Amersham Pharmacia) and so forth. Examples of the vector for the latter expression as a fusion protein include pMAL (New England Bio Lab) for an MBP fusion protein, pGEX (Amersham Pharmacia Biotech) for a GST fusion protein, pCAL (Stratagene) for a fusion protein with a calmodulin-binding peptide, pTrcFus (Invitrogen) for a fusion protein with thioredoxin and pTrcHis (Invitrogen) for a fusion protein with His-tag. Further, these vectors can be appropriately modified and used. Further, as an expression scheme, a method of accumulating the protein as a granule in microbial cells can be used, but the protein can also be accumulated or secreted as a soluble type protein.

Further, an expression system using cells of the prepared mutant protein gene can be constructed by using animal cells, insect cells or the like as a host and incorporating the gene coding for the protein into a vector having a promoter that can be expressed in the host to attain expression.

Refolding of a protein obtained in a form not having the activity can be performed as follows, in which the protein is converted into a form having the activity by cross-linking disulfide bonds in a molecule. First, the granular or soluble type protein that does not have the activity is dissolved in a solution containing a protein-denaturing agent such as guanidine hydrochloride or urea. The protein-denaturing agent can be used at any concentration so long as the protein is dissolved. However, for example, it can be used in the range of from 1 M to a saturated concentration, preferably, from 2 M to 8 M. pH of the solution is not limited, but it is preferably in the range of from 7 to 12, in which cleavage and bonding of a disulfide bond readily occur. The temperature of the solution is not also particularly limited, but it is preferably in the range from 0 to 40° C. A disulfide bond of the protein may be cleaved beforehand by using a reducing agent, but this is not essential. A substance containing Cys such as glutathione, a reducing agent such as dithiothreitol, an enzyme such as a protein disulfide isomerase or the like can also be added during the refolding process.

Further, in order to modify the obtained protein with polyoxyalkylpolyol, a polyoxyalkylpolyol that reacts with an amino group, carboxyl group, thiol group or the like can be added so that it binds to the protein after or during the refolding of the protein as described above. As a specific example of the polyoxyalkylpolyol, polyethylene glycol can be mentioned. Specific examples of the method for binding it to a protein include a method of reacting with a thiol group of Cys.

The above protein having the activity produced by bacteria or cells or the above protein converted into a form of having the activity by refolding can be purified by a combination of widely used chromatography such as ion exchange, gel filtration or reverse phase chromatography, electrophoresis, precipitation operation such as salting out, desalting operation, concentration operation and so forth.

<3> Drug Comprising Protein of Present Invention as Active Ingredient

The protein of the present invention can be utilized as an antithrombotic drug. Since the protein of the present invention is imparted with improvements such as (1) an increased binding activity to its target (glycoprotein Ib), (2) increased half-life/drug efficacy retention in blood and (3) decreased antigenicity compared with a protein before the improvement, it can be used as an anti-inflammatory drug and analgesic drug based on platelet adhesion in addition to a more effective antithrombotic drug.

The protein of the present invention in a drug comprising the protein of the present invention as an active ingredient may be used as it is or as a pharmaceutically acceptable salt thereof. The protein can be used as each alone or as a mixture of two or more kinds of the protein. Other active ingredients may also be added. Usually, it may be mixed with other materials for use in conventional pharmaceutical preparations, for example, ingredients including proteins such as serum albumin, surfactants, salts for a buffering action and osmotic adjustment, carriers and excipients to prepare a pharmaceutical composition.

Examples of the dosage form include a tablet, capsule, subtilized granule, syrup, suppository, ointment, injection, eye drop and so forth. Among these, injection is preferred. As the administration method, any of methods such as intravenous administration, subcutaneous administration, intramuscular administration, oral administration, instillation and enteral administration can be used, but intravenous administration, subcutaneous administration, intramuscular administration and so forth are preferred among them.

As for dose for an animal or human, a dose in the range from 0.1 μg/kg to 100 mg/kg as the amount of the protein of the present invention can usually be expected to provide the desired effect, and a dose that can provide the optimal drug efficacy can be selected within this range.

EXAMPLES

Hereafter, the present invention will be explained in more detail with reference to the following examples.

Example 1

Determination of Three-dimensional Structure of CHH-B α-chain Protein (AS1051-Ala)

(1) Construction of CHH-B α-chain Protein (AS1051-Ala) Expression System Using *Escherichia coli*

An expression system using *Escherichia coli* for the CHH-B α-chain protein wherein the Cys residue in position 81 was mutated to Ala (AS1051-Ala) was constructed by using the *E. coli* HB101/pCHA1 strain (*E. coli* AJ13023) harboring pCHA1 (deposited at the National Institute of Bioscience and Human-Technology, Agency of Industrial Science and Technology, Ministry of International Trade and Industry (postal code: 305-8566, 1–3, Higashi 1-chome, Tsukuba-shi, Ibaraki-ken, Japan) as an international deposition under the provisions of the Budapest Treaty on Aug. 12, 1994 and given an accession number of FERM BP-4781) as follows. The nucleotide sequence of the gene coding for the protein contained in pCHA1 that originates in *Crotalus horridus horridus* and contains AS1051 (its amino acid sequence is shown as SEQ ID NO: 1 in Sequence Listing) is shown as SEQ ID NO: 2 and the amino acid sequence of the encoded protein is shown as SEQ ID NO: 3.

First, a mutation was introduced into the AS1051 gene by the site-specific nucleotide sequence mutation method described in PCR Protocols (Academic Press edition) as follows so that a Cys residue (Cys in position 81 in SEQ ID NO: 1) not involved in a disulfide bond in the AS1051 peptide should be replaced with Ala. PCR was performed by using pCHA1 as a template and primers ASBN (SEQ ID NO: 4) and ASAlaR (SEQ ID NO: 5) or primers ASH (SEQ ID NO: 6) and ASAlaF (SEQ ID NO: 7). Each reaction product was subjected to agarose gel electrophoresis and an amplified DNA fragment was extracted from the gel. The second PCR was performed by using each DNA fragment as a template and the primers ASBN and ASH to prepare a mutant gene. The PCR-amplified DNA was subjected to agarose gel electrophoresis and DNA of 400 base pairs was extracted from the gel. This DNA was digested with restriction enzymes BamHI and HindIII. This DNA fragment was ligated with a plasmid pUC18 (Takara Shuzo) digested with the restriction enzymes BamHI and HindIII by using a Ligation Kit (Takara Shuzo). The *E. coli* JM109 strain was transformed with the obtained plasmid by the competent cell method and cultured on an ampicillin-containing plate at 37° C. for 16 hours to select a transformant.

A plasmid was prepared from the obtained transformant by the alkaline SDS method. Construction of the target plasmid was confirmed by determining the nucleotide sequence by using M13M4 and M13RV primers (both from Takara Shuzo) and a 377PRISM DNA sequencer (Perkin-Elmer). The prepared plasmid was designated as pUCASAla. The plasmid pUCASAla was digested with restriction enzymes NcoI and HindIII and subjected to agarose gel electrophoresis to separate and purify DNA of 400 base pairs. This DNA was ligated with a product obtained by digesting an expression vector pTrcHisA (Invitrogen) with the restriction enzymes NcoI and HindIII by using the Ligation Kit. The *E. coli* JM109 strain was transformed with the obtained plasmid by the competent cell method and cultured on an ampicillin-containing plate at 37° C. for 16 hours to select a transformant. The expression vector contained in this transformant was designated as pTrcASAla.

(2) Preparation of Active Substance by Refolding of AS1051-Ala

The transformant *E. coli* JM109 strain harboring the expression vector pTrcASAla for AS1051-Ala was cultured at 37° C. in L-broth (1% Bacto trypton, 0.5% yeast extract, 0.5% sodium chloride, 100 µg/ml ampicillin sodium) by using a Sakaguchi flask. IPTG (isopropyl-β-thiogalactopyranoside) was added at 10 mM when the turbidity (measured at 660 nm, ditto for the following examples) reached 0.5 and further cultured at 37° C. for 4 hours. Microbial cells were collected and washed by centrifugation. Then, the microbial cells were suspended in 0.5 M EDTA solution. Lysozyme was added thereto and the mixture was then left standing at room temperature for 1 hour. The suspension of the microbial cells was disrupted by an ultrasonicator (200 W, 5 minutes), and the disrupted suspension was centrifuged to obtain granules (inclusion bodies) as precipitates.

The obtained granules were dissolved in 0.5 M Tris-HCl buffer (pH 8.5) containing 7 M guanidine hydrochloride and 10 mM EDTA. Then, distilled water was added in a volume of 2.5 times the solution and the mixture was left standing overnight at 4° C. The solution was dialyzed against 0.9% saline by using a Spectra/Por 1 dialysis membrane (Spectra) to remove guanidine hydrochloride. To the solution after the dialysis, 1/9 volume of 0.5 M ammonium acetate buffer (pH 4.5) was added, and the mixture was loaded on an ion exchange column using CM-TOYOPEARL 650S (2.6×40 cm) and eluted with Elution solution A (50 mM ammonium acetate buffer (pH 4.5)) and Elution solution B (0.5 M ammonium acetate buffer (pH 6.4)). The elution was performed with a solution composed of Elution solution A and B (A:B=75:25, volume ratio, ditto in the following examples) for 20 minutes, and then with a linear gradient of from A:B=75:25 to A:B=50:50 for 30 minutes. Thus, an eluted fraction containing purified AS1051-Ala was obtained.

AS1051-Ala has a structure in which Met is added to the N-terminus of the amino acid sequence of SEQ ID NO: 1 and Cys81 is replaced with Ala.

(3) Determination of Three-dimensional Structure of AS1051-Ala by X-ray Crystal Structure Analysis The purified AS1051-Ala was crystallized by the vapor diffusion method in sitting drops method as follows. A mixed solution of 5 µl each of a buffer (reservoir solution) composed of 0.1 M NaHepes (pH 7.3), 12% PEG4K (polyethylene glycol having a molecular weight of 4000), 22% 2-propanol, 10 mM $CaCl_2$ and 10 mg/ml of AS1051-Ala solution was placed in a cavity of a bridge provided over a well filled with 500 µl of the reservoir solution and left standing in the sealed well at 20° C. Tabular crystals in the maximum size of 0.8×0.2×0.15 mm were obtained in about 10 days to 2 weeks. To obtain X-ray diffraction data, the crystals were transferred into a buffer containing 0.1 M NaHepes (pH 7.3), 12% PEG4K and 22% 2-propanol. X-ray diffraction data up to 2.5 Å resolution were collected at room temperature by using an X-ray diffractometer R-AXIS IIc (Rigaku Corporation) to determine crystallographic parameters. The space group was $β2_12_12$, and the cell parameters were a=44.7 Å, b=66.7 Å and c=46.8 Å. The solvent content of the crystals was estimated to be 47%. Further, 1.8 Å resolution X-ray data were collected by using a Weissenberg camera for macromolecules installed in BL6A of a synchrotron radiation facility in the High Energy Physics Laboratory.

The crystal structure analysis was performed by the heavy atom isomorphous replacement method. The crystals were immersed in 1 to 10 mM solutions of heavy metal salts, and X-ray data were measured by using the R-AXIS IIc to screen heavy atom isomorphous crystals. As a result, it was revealed that X-ray data of the crystals immersed in solutions of three heavy atom salts, cis-Pt(ethylenediamine)$Cl_2$, cis-Pt$(NH_3)_2Cl_2$ and trans-Pt$(NH_3)_2Cl_2$ showed significant differences from the X-ray data of the native crystals. In particular, the cis-Pt(ethylenediamine)$Cl_2$ showed an easily interpretable difference Patterson map. The coordinates of the sole mercury binding site of the cis-Pt(ethylenediamine)$Cl_2$ were obtained by using a program RSPS. These coordinates were refined by using program MLPHARE and used to calculate the phases. The mercury binding sites of the two other heavy metal salts, i.e., cis-Pt$(NH_3)_2Cl_2$ and trans-Pt$(NH_3)_2Cl_2$, were obtained by using these phases. The three heavy atom parameters of the heavy atom isomorphous replaced crystals were simultaneously refined by using MLPHARE, and then solvent flattering and histogram matching were performed by using program DM to improve the phases. An anomalous dispersion effect of the cis-Pt (ethylenediamine)$Cl_2$ was also used. The electron density map at a resolution of 3 Å calculated by using the phases improved as described above had good quality sufficient to easily identify α helices or β strands.

The α carbon chains were constructed by using program QUANTA (MSI). First, a region from Leu2 to Leu72 and a region from Glu94 to Arg124 were constructed. It was difficult to interpret the region from Arg73 to Phe93 at this stage. The side chains of Leu2 to Leu72 and Glu94 to Arg124 were added and then refined by using program X-PLOR (MSI). Then, the model was corrected by using QUANTA and refined by using X-PLOR, which were repeated until the R value decreased to 0.304 at a resolution of 3 Å. At this point, the phases calculated from the model and the phases calculated from the heavy atom isomorphous replaced crystals were combined by using program SIGMAA. By using the (Fo-Fc) map obtained as described above, the region from Arg73 to Phe93 could be constructed as a polyalanine model. Further, the side chains of this region were added stepwise by alternately using QUANTA and X-PLOR. In this process, the resolution was increased up to 1.8 Å. When the resolution exceeded 2.5 Å, data obtained by using R-AXIS IIc was switched to data obtained by using synchrotron radiation. Further, the structure was corrected and water molecules were included. Finally, a model with an R value of 0.187 was obtained for data in a resolution range between 6 and 1.8 Å (FIG. 1). The final model contained 123 residues of Leu2 to Arg124 and 53 water molecules. N-terminal Met, Asp1, Pro125, Arg126, and side chains of Arg73, Val74, Gln75, Glu87, Phe93 and Arg105 were not observed. The rms value, which is a value of deviation from the ideal bond length, was 0.019 Å, while that of the bonding angle was 2.898 Å. Further, the average temperature factor of the main chain atom was 23 Å$^2$ while that of the side chain atom was 28 Å$^2$. When a Ramachandran plot was created by using program PROCHECK, it was shown that 96% of residues other than Gly were located in the most favored region and that 3% was located in the additionally allowed region. The programs RSPS, MLPHARE, DM, SIGMAA and PROCHECK are available from CCP4 (CCP4, Acta Crystallogr. D, 50, 760–763).

Example 2
Preparation of Loop Structure-deleted AS1051 Protein (AS1051-G4)
(1) Examination of Central Loop Structure There exists a long loop projecting to a solvent between β2 and β3 as shown in FIG. 1. This loop was designated as a central loop. The average temperature factor of the α carbon atoms in the central loop containing 20 residues of Val74 to Phe93 was 37.4 Å$^2$, which was markedly higher than the average temperature factor of the α carbon atoms other than those of the central loop, 20.2 Å$^2$. This indicated that flexibility of the central loop was extremely high. The central loop includes Ala81, a residue corresponding to Cys81 in the wild-type AS1051, which is involved in an intermolecular S—S bond with the CHH β-chain. Therefore, while the central loop is considered to play an important role in formation of a dimer with the β-chain, it is considered that, when the α-chain (AS1051) exists solely, a hydrophobic residue is exposed to the solvent and easily recognized as an antigen. Therefore, to confirm whether antigenicity can be decreased by removing the central loop, a mutant deficient in the central loop was prepared. Since the distance between the α carbon atoms of Val74 and Phe93 was 16.1 Å, it was considered that the central loop could be replaced with a peptide of four residues. As the four amino acid residues, it was considered appropriate to use glycine, which does not have a β carbon atom and has little restriction by a dihedral angle (φ/ψ value). The central loop was replaced with four Gly residues (G4) by using the program QUANTA (MSI), and the obtained structure was optimized by molecular dynamics calculation by using the program X-PLOR (MSI). At this time, a restriction in the X-ray term was applied so that the structure other than G4 should not be significantly changed. When a Ramachandran plot of the optimized structure was created by using the program PROCHECK, it was demonstrated that the four Gly residues and residues before and after them were located in the most preferable region. That is, it was indicated that the mutant (AS1051-G4) in which the central loop is replaced with the four Gly residues could have a structure without distortion.
(2) Construction of Expression Vector of AS1051-G4 for *Escherichia coli*

The gene coding for a mutant peptide AS1051-G4 having the amino acid sequence of SEQ ID NO: 1 of the AS1051 peptide wherein 20 amino acids from the 74th Val to the 93rd Phe were replaced with four Gly residues was prepared by using the cloned gene. DNA primers for preparing the mutant gene were synthesized by the PCR method. As primers containing the mutated region, G4F (SEQ ID NO: 8) and its complementary sequence, G4R (SEQ ID NO: 9), were prepared. Further, a primer containing an NcoI recognition sequence (ASBN: SEQ ID NO: 4) was used as the 5' end primer so that the 5' end of the amplified fragment should have the NcoI site and thus the mutant gene to be prepared could be incorporated into an expression vector in the subsequent process. Further, this primer had a nucleotide sequence ATG (nucleotide numbers 10 to 12 in SEQ ID NO: 4), which was a translation initiation codon, before a codon of the N-terminal amino acid AS1051 peptide, i.e., aspartic acid, on the 5' end side. This initiation codon overlapped the NcoI recognition sequence (nucleotide numbers 8 to 13 in SEQ ID NO: 4). As the 3' end primer, a primer containing a HindIII recognition sequence (SEQ ID NO: 6, HindIII recognition sequence corresponds to nucleotide numbers 4 to 9) was used. First, PCR was performed by using pCAH1 as a template and the primers ASBN and G4R with a cycle of reactions at 94° C. for 15 seconds, at 35° C. for 1 minute and at 72° C. for 2 minutes, which was repeated 25 times. Similarly, PCR was performed by using pCAH1 as a template and the primers ASH and G4R with a cycle of reactions at 94° C. for 15 seconds, at 35° C. for 1 minute and at 72° C. for 2 minutes, which was repeated 25 times. Each PCR reaction mixture was subjected to agarose gel electrophoresis. The amplified DNA fragments of 250 base pairs and 130 base pairs were collected from the gel by using EASYTRAP (Takara Shuzo). As the second PCR, PCR was performed by using the DNA fragments of 250 base pairs and 130 base pairs collected as described above and the ASBN primer and ASH primer. PCR was performed with a cycle of reactions at 94° C. for 15 seconds, at 35° C. for 1 minute and at 72° C. for 2 minutes, which was repeated 25 times. The PCR reaction mixture was subjected to a phenol/chloroform treatment to inactivate Taq polymerase. The amplified DNA fragment of 400 base pairs was purified by ethanol precipitation and digested with restriction enzymes BamHI and HindIII. This DNA fragment was ligated with a plasmid pUC18 (Takara Shuzo) digested with restriction enzymes BamHI and HindIII by using a Ligation Kit (Takara Shuzo). The *E. coli* JM109 strain was transformed with the obtained plasmid by the competent cell method and cultured on an ampicillin-containing plate at 37° C. for 16 hours to select a transformant. A plasmid was prepared from a grown transformant by the alkaline SDS method. Construction of the target plasmid was confirmed by determining the nucleotide sequence by using the M13M4 and M13RV primers (both from Takara Shuzo) and a 377PRISM DNA sequencer (Perkin-Elmer). The prepared mutant plasmid was designated as pUCASG4BNH.

The plasmid pUCASG4BNH was digested with restriction enzymes NcoI and HindIII and subjected to agarose gel electrophoresis to separate and purify DNA of 350 base pairs. This DNA was ligated with a product obtained by digesting an expression vector pTrcHisA (Invitrogen) with restriction enzymes NcoI and HindIII by using the Ligation Kit. The *E. coli* JM109 strain was transformed with the obtained plasmid by the competent cell method and cultured on an ampicillin-containing plate at 37° C. for 16 hours to select a transformant. The expression vector obtained as described above was designated as pTrcASG4. The expressed and produced AS1051-G4 peptide has a structure in which Met is added to the N-terminus of the amino acid sequence of SEQ ID NO: 10.

(3) Acquisition of AS1051-G4

The transformant *E. coli* JM109 strain harboring the expression vector pTrcASG4 for AS1051-G4 was cultured at 37° C. in L-broth (1% Bacto trypton, 0.5% yeast extract, 0.5% sodium chloride, 100 μg/ml ampicillin sodium) by using a Sakaguchi flask. IPTG (isopropyl-β-thiogalactopyranoside) was added at 10 mM when the turbidity reached 0.5 and further cultured at 37° C. for 4 hours. The microbial cells were collected and washed by centrifugation. Then, the microbial cells were suspended in a 0.5 M EDTA solution. Lysozyme was added thereto and the mixture was left standing at room temperature for 1 hour. The suspension of the microbial cells was disrupted by an ultrasonicator (200 W, 5 minutes) and the disrupted suspension was centrifuged to obtain granules (inclusion bodies) as precipitates.

The obtained granules were dissolved in 0.5 M Tris-HCl buffer (pH 8.5) containing 7 M guanidine hydrochloride and 10 mM EDTA. Then, distilled water was added in a volume of 2.5 times the solution and the mixture was left standing overnight at 4° C. The solution was dialyzed against 0.9% saline by using a Spectra/Por 1 dialysis membrane (Spectra) to remove guanidine hydrochloride. To the solution after the dialysis, 1/9 volume of 0.5 M ammonium acetate buffer (pH 4.5) was added, and the mixture was loaded on an ion exchange column using CM-TOYOPEARL 650S (2.6×40 cm) and eluted with Elution solution A (50 mM ammonium acetate buffer (pH 4.5)) and Elution solution B (0.5 M ammonium acetate buffer (pH 6.4)). The elution was performed with a solution composed of Elution solution A and B (A:B=70:30) for 20 minutes, and then with a linear gradient of from A:B=70:30 to A:B=40:60 for 30 minutes. Thus, an eluted fraction containing purified AS1051-G4 was obtained.

Example 3

Structure of Loop Structure-deleted AS1051 Protein (AS1051-G4)

SDS electrophoresis revealed that the molecular weight of the obtained AS1051-G4 was 12 kDa, which was about 3 kDa lower than that of the aforementioned AS1051-Ala (15 kDa).

Figure 2:
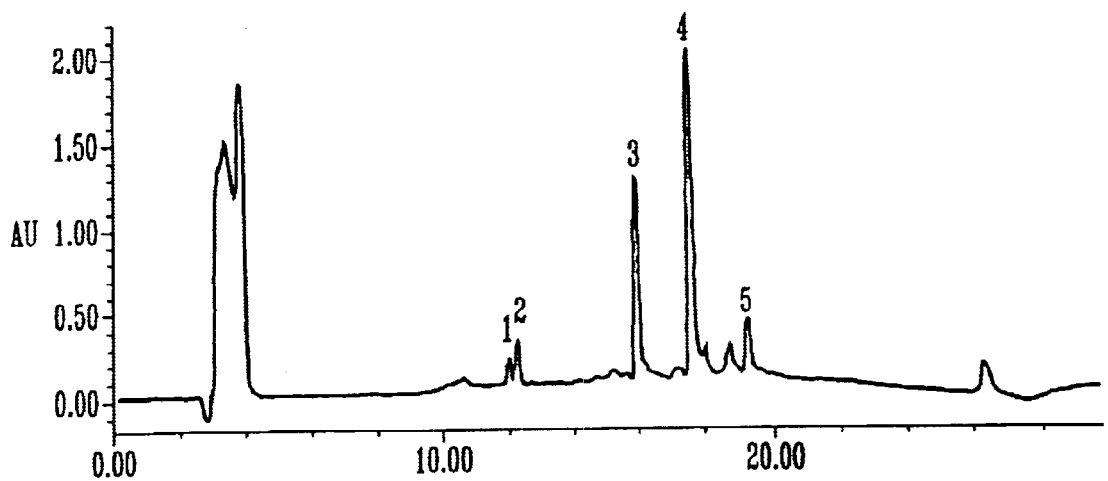

Subsequently, the linkage scheme of a disulfide bond of Cys in AS1051-G4 was determined as follows. AS1051-G4 (100 μg) was digested with lysyl endopeptidase (5 μg, Wako Pure Chemical Industries) in 0.1 M Tris-HCl buffer (pH 8.5) containing 2 mM EDTA at 37° C. for 5 hours and fractionated by high performance liquid chromatography using a reverse phase column (Vydac 218TP54, Vydac). Elution was performed with a linear gradient of water/acetonitrile containing 0.1% trifluoroacetic acid (TFA) (acetonitrile concentration of from 0 to 50% for 10 minutes, acetonitrile concentration of from 50% to 100% for 5 minutes). Thus, digested peptide chains were obtained as Peaks 1 to 5 (FIG. 2). The amino acid sequence of each peptide chain was analyzed by using a protein sequencer Model 476A (Applied Biosystems). Since two Cys residues are contained in the peptide chain of Peak 3, it was concluded that these two Cys residues were coupled to form a disulfide bond. Further, it was found that Peak 4 was composed of total three peptide chains, wherein two peptide chains containing one Cys residue and one peptide chain containing two Cys residues were coupled through disulfide bonds. The peptide chains of this Peak 4 were further digested with V8 protease (5 μg, Wako Pure Chemical Industries) in 10 mM ammonium carbonate buffer at 25° C. for 24 hours and fractionated by high performance liquid chromatography using a reverse phase column (Pegasil ODS-II, Senshu Kagaku). Elution was performed with a linear gradient of water/acetonitrile containing 0.1% TFA (acetonitrile concentration of from 0 to 50% for 20 minutes). Thus, peptide chains obtained by digestion were prepared and their amino acid sequences were analyzed. As a result, it was found that the peptides of Peak 4 had such a disulfide bond as shown in FIG. 2. The scheme of disulfide bond in AS1051-G4 determined as described above was the same as in the reported AS1051 (N. Fukuchi et al., WO95/08573) or other similar proteins originating from snake venom (Y. Fujimura et al., Thromb. Haemost., 76, pp.633–639 (1996)).

Example 4

Preparation of Protein Containing Single Amino Acid Mutation

Proteins were prepared in which amino acids of AS1051-G4 prepared in Example 2 were mutated as shown in Table 1. The amino acid numbers used in the table correspond to the amino acid numbers in SEQ ID NO: 1.

TABLE 1

| Mutant protein | Amino acid to be mutated | Amino acid after mutation |
| --- | --- | --- |
| M7-G4 | Lys20 | Ala20 |
| M8-G4 | Asp54 | Ala54 |
| M9-G4 | Tyr58 | Ala58 |
| M10-G4 | Lys61 | Ala61 |
| M11-G4 | Glu62 | Ala62 |
| M12-G4 | Tyr63 | Ala63 |
| M13-G4 | Arg66 | Ala66 |
| M14-G4 | Tyr67 | Ala67 |
| M15-G4 | Arg100 | Ala100 |
| M16-G4 | Asp101 | Ala101 |
| M17-G4 | Arg103 | Ala103 |
| M18-G4 | Arg105 | Ala105 |
| M19-G4 | Glu106 | Ala106 |
| M20-G4 | Phe108 | Ala108 |

By using the expression plasmid pTrcASG4 for AS1051-G4 as a template and one of combinations of primers M7F (SEQ ID NO: 11) and M7R (SEQ ID NO: 12), M8F (SEQ ID NO: 13) and M8R (SEQ ID NO: 14), M9F (SEQ ID NO: 15) and M9R (SEQ ID NO: 16), MIOF (SEQ ID NO: 17) and M10R (SEQ ID NO: 18), M11F (SEQ ID NO: 19) and M11R (SEQ ID NO: 20), M12F (SEQ ID NO: 21) and M12R (SEQ ID NO: 22), M13F (SEQ ID NO: 23) and M13R (SEQ ID NO: 24), M14F (SEQ ID NO: 25) and M14R (SEQ ID NO: 26), M15F (SEQ ID NO: 27) and M15R (SEQ ID NO: 28), M16F (SEQ ID NO: 29) and M16R (SEQ ID NO: 30), M17F (SEQ ID NO: 31) and M17R (SEQ ID NO: 32), M18F (SEQ ID NO: 33) and M18R (SEQ ID NO: 34), M19F (SEQ ID NO: 35) and M19R (SEQ ID NO: 36), and M20F (SEQ ID NO: 37) and M20R (SEQ ID NO: 38), PCR was performed according to the protocol attached to a QuickChange™ Site-Directed Mutagenesis Kit (Stratagene) to obtain plasmids pTrcM7G4, pTrcM8G4, pTrcM9G4, pTrcM10G4, pTrcM11G4, pTrcM12G4, pTrcM13G4, pTrcM14G4, pTrcM15G4, pTrcM16G4, pTrcM17G4, pTrcM18G4, pTrcM19G4 and pTrcM20G4 expressing mutant proteins M7-G4, M8-G4, M9-G4, M10-G4, M11-G4, M12-G4, M13-G4, M14-G4, M15-G4, M16-G4, M17-G4, M18-G4, M19-G4 and M20-G4, respectively.

The transformant *E. coli* JM109 strains harboring the prepared expression plasmids pTrcM8G4 to pTrcM20G4 were each cultured at 37° C. in L-broth (1% Bacto trypton, 0.5% yeast extract, 0.5% sodium chloride, 100 μg/ml ampicillin sodium). IPTG (isopropyl-β-thiogalactopyranoside) was added at 0.5 mM when the turbidity reached 0.5 and further cultured at 37° C. for 4 hours. The microbial cells were collected and washed by centrifugation. Then, the microbial cells were suspended in a 0.5 M EDTA solution. Lysozyme was added thereto and the mixture was left standing at room temperature for 1 hour. The suspension of the microbial cells was disrupted by an ultrasonicator (200 W, 10 minutes) and the disrupted suspension was centrifuged to obtain granules (inclusion bodies) as precipitates.

The obtained granules were dissolved in 0.5 M Tris-HCl buffer (pH 8.5) containing 7 M guanidine hydrochloride and 10 mM EDTA. Then, 5 mM reduced type glutathione solution and 0.5 mM oxidized type glutathione solution were added in a volume of 2.5 times the solution and the mixture was left standing overnight at 4° C. The solution was dialyzed against 0.9% saline by using a Spectra/Por 1 dialysis membrane (Spectra) to remove guanidine hydrochloride. To the solution after the dialysis, 1/9 volume of 0.5 M ammonium acetate buffer (pH 4.5) was added, and the mixture was loaded on an ion exchange column using TSK-gel CM-5PW (1.0×7.5 cm) and eluted with Elution solution A (50 mM ammonium acetate buffer (pH 4.5)) and Elution solution B (0.5 M ammonium acetate buffer (pH 6.4)). The elution was performed with a solution composed of Elution solutions A and B (A:B=100:0) for 5 minutes, and then with a linear gradient of from A:B=100:0 to A:B=0:100 for 30 minutes. Thus, purified M8-G4 to M20-G4 were obtained. The proteins were quantified by comparing the elution peak area at 280 nm obtained by reverse phase HPLC using Pegasil ODS-300 (4.6×250 mm, Senshu Kagaku) by using AS1051-Ala (see Example 1) and AS1051-G4 (see Example 2) quantified beforehand with a Bio-Rad Protein Assay (Bio-Rad) as standards.

Example 5

Glycoprotein Ib/von Willebrand Factor Binding Inhibitory Activity of Loop Structure-deleted Protein (AS1051-G4) and Protein Containing Amino Acid Mutation The glycoprotein Ib/von Willebrand factor binding inhibitory activity of the loop structure-deleted protein (AS1051-G4) prepared in Example 2 and the proteins having a single amino acid mutation (M7 to M20) prepared in Example 4 was determined in the same manner as in the method of N. Fukuchi et al. (WO99/54360, Example 7 in the specification). That is, 50 µl of TBS (Tris-buffered saline, 20 mM Tris-HCl (pH 7.4), 0.15 M NaCl) solution containing von Willebrand factor (2.5 µg/ml) was added to each well of a 96-well plate and immobilized overnight at 4° C. as a solid phase. Then, the wells were washed with TBS (150 µl) once and blocked with TBS containing 5% BSA for 3 hours. The plate was washed with TBS (150 µl) twice. To 25 µl of assay buffer (Assay Buffer, 1244-106, Wallac), a diluted protein whose inhibitory activity was to be determined was added. Then, 25 µl of assay buffer containing a chimera protein (100 ng/ml) of europium (Eu) labeled human glycoprotein Ib α-chain and a mouse IgG2a Fc region, and botrocetin (500 ng/ml) were added thereto and the mixture was left at room temperature for about 3 hours. The plate was washed with 150 µl of TBS containing 0.05% Tween-20 five times. Then, 100 µl of fluorescence enhancing buffer (Enhancement solution, 1244-104, Wallac) was added and the plate was shaken for 1 minute and then the europium (Eu) amount was measured by using a 1420ARVO multilabel counter (Wallac) (measurement time: 1 second). $IC_{50}$ values for glycoprotein Ib/von Willebrand factor binding inhibition of the respective mutant proteins are shown in Table 2.

TABLE 2

| Protein | $IC_{50}$ value (ng/ml) |
|---|---|
| AS1051-Ala | 70.4 |
| AS1051-G4 | 57.8 |
| M7-G4 | 45.4 |
| M8-G4 | 28.7 |
| M9-G4 | 1607 |
| M10-G4 | 701.9 |
| M11-G4 | 56.0 |
| M12-G4 | 347.2 |
| M13-G4 | 294.3 |
| M14-G4 | 1091 |
| M15-G4 | 234.7 |
| M16-G4 | 10.6 |
| M17-G4 | 14327 |
| M18-G4 | 1292.6 |
| M19-G4 | 26.9 |
| M20-G4 | 483.0 |

From the above data, it was found that the inhibitory activity on glycoprotein Ib/von Willebrand factor binding greatly decreased by the mutations of Tyr58 (M9-G4), Tyr67 (M14-G4), Arg103 (M17-G4), Arg105 (M18-G4) and Phe108 (M20-G4) to Ala and, in particular, the activity was most markedly decreased (about 1/250) by the mutation of Arg103 (M17-G4). It was also observed that the glycoprotein Ib/von Willebrand factor binding inhibitory activity was increased by the mutations of Asp54 (M8-G4), Asp101 (M16-G4) and Glu106 (M19-G4) to Ala. According to the crystal structure data, the α carbons of all the three residues, of which mutation increased the activity, were within 10 Å from the α carbon of Arg103, of which mutation most markedly decreased the activity and which was considered to be most important for the glycoprotein Ib/von Willebrand factor binding inhibitory activity.

Example 6

Preparation of Highly Active Proteins Containing a Plurality of Amino Acid Mutations and Their Activity (1) Preparation of Mutant Proteins Proteins containing a plurality of amino acid mutations were prepared in the same manner as in the method for preparing the proteins containing a single amino acid mutation. Designations of mutant genes and their mutations are shown in Table 3. The amino acid numbers used in the table correspond to the amino acid numbers used in SEQ ID NO: 1.

TABLE 3

| Mutant protein | Amino acid to be mutated | Amino acid after mutation |
|---|---|---|
| M21 | Asp54, Asp101, Glu106 | Ala54, Asn101, Gln106 |
| M22 | Asp54, Asp101, Glu106 | Ala54, Ala101, Ala106 |
| M23 | Asp54, Asp101 | Asn54, Ala101 |
| M24 | Asp54, Asp101 | Ala54, Ala101 |
| M25 | Asp101, Glu106 | Ala101, Gln106 |
| M26 | Asp101, Glu106 | Ala101, Ala106 |

PCR was performed by using the expression plasmid pTrcM8G4 for M8-G4 as a template, primers M21F (SEQ ID NO: 39) and M21R (SEQ ID NO: 40) or primers M22F (SEQ ID NO: 41) and M22R (SEQ ID NO: 42) and a QuickChange™ Site-Directed Mutagenesis Kit (Stratagene) to obtain expression plasmids pTrcM21G4 and pTrcM22G4 for the mutant protein M21-G4 and M22-G4, respectively. Further, PCR was performed by using the expression plasmid pTrcM16G4 of M16-G4 as a template, primers M23F (SEQ ID NO: 43) and M23R (SEQ ID NO: 44), primers M8F (SEQ ID NO: 13) and M8R (SEQ ID NO: 14), primers M25F (SEQ ID NO: 45) and M25R (SEQ ID NO: 46) or primers M19F (SEQ ID NO: 35) and M19R (SEQ ID NO: 36), and the QuickChange™ Site-Directed Mutagenesis Kit (Stratagene) to obtain expression plasmids pTrcM23G4, pTrcM24G4, pTrcM25G4 and pTrcM26G4 for the mutant proteins M23-G4, M24-G4, M25-G4 and M26-G4, respectively.

The transformant *E. coli* JM109 strains harboring each of the expression plasmids pTrcM21G4, pTrcM22G4, pTrcM23G4, pTrcM24G4, pTrcM25G4 and pTrcM26G4 prepared as described above were each cultured at 37° C. in L-broth (1% Bacto trypton, 0.5% yeast extract, 0.5% sodium chloride, 100 μg/ml ampicillin sodium) by using Sakaguchi flasks. IPTG (isopropyl-β-thiogalactopyranoside) was added at 10 mM when the turbidity reached 0.5 and further cultured at 37° C. for 4 hours. The microbial cells were collected and washed by centrifugation. Then, the microbial cells were suspended in a 0.5 M EDTA solution. Lysozyme was added thereto and the mixture was left standing at room temperature for 1 hour. The suspension of the microbial cells was disrupted by an ultrasonicator (200 W, 5 minutes) and the disrupted suspension was centrifuged to obtain granules (inclusion bodies) as precipitates.

The obtained granules were dissolved in 0.5 M Tris-HCl buffer (pH 8.5) containing 7 M guanidine hydrochloride and 10 mM EDTA. Then, distilled water was added in a volume of 2.5 times the solution and the mixture was left standing overnight at 4° C. The solution was dialyzed against 0.9% saline by using a Spectra/Por 1 dialysis membrane (Spectra) to remove guanidine hydrochloride. To the solution after the dialysis, 1/9 volume of 0.5 M ammonium acetate buffer (pH 4.5) was added, and the mixture was loaded on an ion exchange column using TSK-gel CM-5PW (1.0×7.5 cm) and eluted with Elution solution A (50 mM ammonium acetate buffer (pH 4.5)) and Elution solution B (0.5 M ammonium acetate buffer (pH 6.4)). The elution was performed with a solution composed of Elution solutions A and B (A:B=100:0) for 5 minutes, and then with a linear gradient of from A:B=100:0 to A:B=0:100 for 30 minutes. Thus, eluted fractions each containing purified M21-G4, M22-G4, M23-G4, M24-G4, M25-G4 or M26G4 were obtained. The protein amount was measured by using AS1051-Ala (see Example 1) and AS1051-G4 (see Example 2) quantified beforehand by using a Protein Assay Kit (BioRad) as standards and comparing peak areas at 280 nm obtained in reverse phase HPLC (high performance liquid chromatography) using Pegasil ODS-300 (4.6×250 mm, Senshu Kagaku).

(2) Measurement of Glycoprotein Ib/von Willebrand Factor Binding Inhibitory Activity Subsequently, the glycoprotein Ib/von Willebrand factor binding inhibitory activity of the proteins containing a plurality of amino acid mutations was measured by using the method described in Example 5. $IC_{50}$ values of glycoprotein Ib/von Willebrand factor binding inhibition of the mutant proteins are shown in Table 4. All the mutant proteins exhibited increase of the glycoprotein Ib/von Willebrand factor binding inhibitory activity, and M23-G4 exhibited the highest inhibitory activity.

TABLE 4

| Protein | $IC_{50}$ value (ng/ml) |
|---|---|
| AS1051-Ala | 46.9 |
| AS1051-G4 | 50.3 |

TABLE 4-continued

| Protein | $IC_{50}$ value (ng/ml) |
|---|---|
| M16-G4 | 14.2 |
| M21-G4 | 14.7 |
| M23-G4 | 9.8 |
| M24-G4 | 11.6 |
| M25-G4 | 11.4 |

Example 7

Preparation of Polyethylene Glycol-modified Proteins and Their Activity (1) Preparation of Polyethylene-glycolated AS1051 that is not Mutated Proteins containing amino acid mutations shown in Example 6 to be polyethylene-glycolated were prepared in the same manner as in the above-described method.

First, to utilize Cys81 of a natural type AS1051 as Cys to be polyethylene-glycolated, an expression gene of AS1051 in which Cys81 was not replaced with Ala (AS1051-WT) was constructed. PCR was performed by using the plasmid pCHA1 containing AS1051 described in Example 1 as a template and primers ASBN (SEQ ID NO: 4) and ASH (SEQ ID NO: 6). The reaction product was subjected to agarose gel electrophoresis to extract DNA of 400 base pairs from the gel. This DNA fragment was digested with restriction enzymes BamHI and HindIII. This DNA fragment was ligated with a plasmid pUC18 (Takara Shuzo) digested with restriction enzymes BamHI and HindIII by using a Ligation Kit (Takara Shuzo). The *E. coli* JM109 strain was transformed with the obtained plasmid by the competent cell method and cultured on an ampicillin-containing plate at 37° C. for 16 hours to select a transformant. A plasmid was prepared from a grown transformant by the alkaline SDS method. Construction of the target plasmid was confirmed by determining the nucleotide sequence by using the M13M4 and M13RV primers (both from Takara Shuzo) and a 377PRISM DNA sequencer (Perkin-Elmer). The prepared plasmid was designated as pUCASWT. The plasmid PUCASWT was digested with restriction enzymes NcoI and HindIII and subjected to agarose gel electrophoresis to separate and purify DNA of 400 base pairs. This DNA fragment was ligated with expression vector pTrcHisA (Invitrogen) digested with restriction enzymes NcoI and HindIII by using the Ligation Kit. The *E. coli* JM109 strain was transformed with the obtained plasmid by the competent cell method and cultured on an ampicillin-containing plate at 37° C. for 16 hours to select a transformant. The expression plasmidcontained in this transformant was designated as pTrcASWT.

The transformant *E. coli* JM109 strain harboring the expression plasmid pTrcASWT for AS1051-Cys was cultured in the same manner as in the method shown in Example 1 to obtain granules (inclusion bodies) as precipitates.

A polyethylene-glycolated AS1051 protein (AS1051-PEG5000) was prepared by using a polyethylene-glycolating reagent having maleimide groups and a molecular weight of about 5000 (Methoxy-PEG-mal, MW 5000, Item No.: M-MAL-5000, Shearwater Polymers) as follows. The AS1051 granules obtained by the culture were dissolved in 0.5 M Tris-HCl buffer (pH 8.5) containing 7 M guanidine hydrochloride and 10 mM EDTA. Then, distilled water was added in a volume 2.5 times the solution and the mixture was left standing overnight at 4° C. Further, to this solution, the aforementioned polyethylene-glycolating reagent was added at a concentration of 0.2 mg/ml and the mixture was left standing at room temperature for 3 hours. The solution was dialyzed against distilled water by using a Spectra/Por 1 dialysis membrane (Spectra) to remove guanidine hydrochloride. To the solution after the dialysis, 1/9 volume of 0.5 M ammonium acetate buffer (pH 4.5) was added, and the mixture was loaded on an ion exchange column using CM-TOYOPEARL 650S (2.6×40 cm) and eluted with Elution solution A (50 mM ammonium acetate buffer (pH 4.5)) and Elution solution B (0.5 M ammonium acetate buffer (pH 6.4)). The elution was performed with a linear gradient of from A:B=80:20 to A:B=70:30 (20 minutes) and then with a linear gradient of from A:B=70:30 to A:B=55:45 (30 minutes). Thus, an eluted fraction containing purified AS1051-PEG5000 was obtained.

A polyethylene-glycolated AS1051 protein (AS1051-PEG20000) was prepared by using a polyethylene-glycolating reagent having a molecular weight of about 20,000 (Methoxy-PEG-mal, MW 20000, Item No.: M-MAL-20000, Shearwater Polymers), which had maleimide groups, as follows. The AS1051 granules obtained by the culture were dissolved in 0.5 M Tris-HCl buffer (pH 8.5) containing 7 M guanidine hydrochloride and 10 mM EDTA. Then, distilled water was added in a volume 2.5 times the solution and the mixture was left standing overnight at 4° C. Further, to this solution, the aforementioned polyethylene-glycolating reagent was added at a concentration of 0.2 mg/ml and the mixture was left standing at room temperature for 3 hours. The solution was dialyzed against distilled water by using a Spectra/Por 1 dialysis membrane (Spectra) to remove guanidine hydrochloride. To the solution after the dialysis, 1/9 volume of 0.5 M ammonium acetate buffer (pH 4.5) was added, and the mixture was loaded on an ion exchange column using CM-TOYOPEARL 650S (2.6×40 cm) and eluted with Elution solution A (50 mM ammonium acetate buffer (pH 4.5)) and Elution solution B (0.5 M ammonium acetate buffer (pH 6.4)). The elution was performed with a linear gradient of from A:B=100:0 to A:B=40:60 (20 minutes) and then with a linear gradient of from A:B=40:60 to A:B=0:100 (30 minutes). Thus, an eluted fraction containing purified AS1051-PEG20000 was obtained.

(2) Structure of AS1051-PEG5000

SDS electrophoresis revealed that the molecular weight of the obtained AS1051-PEG5000 was 25 kDa, about 10 kDa larger than that of the AS1051-Ala that was not polyethylene-glycolated (15 kDa). Since polyethylene glycol is observed with a size twice as large as the original molecular weight due to hydration in SDS electrophoresis, it was confirmed that one molecule of polyethylene glycol (molecular weight of about 5000) bonded to one molecule of AS1051-PEG5000. Further, a band of the AS1051-PEG20000 was observed at about 55 kDa, and it was confirmed that one molecule of polyethylene glycol (molecular weight of 20,000) bonded to one molecule of AS1051-PEG20000.

Figure 3:
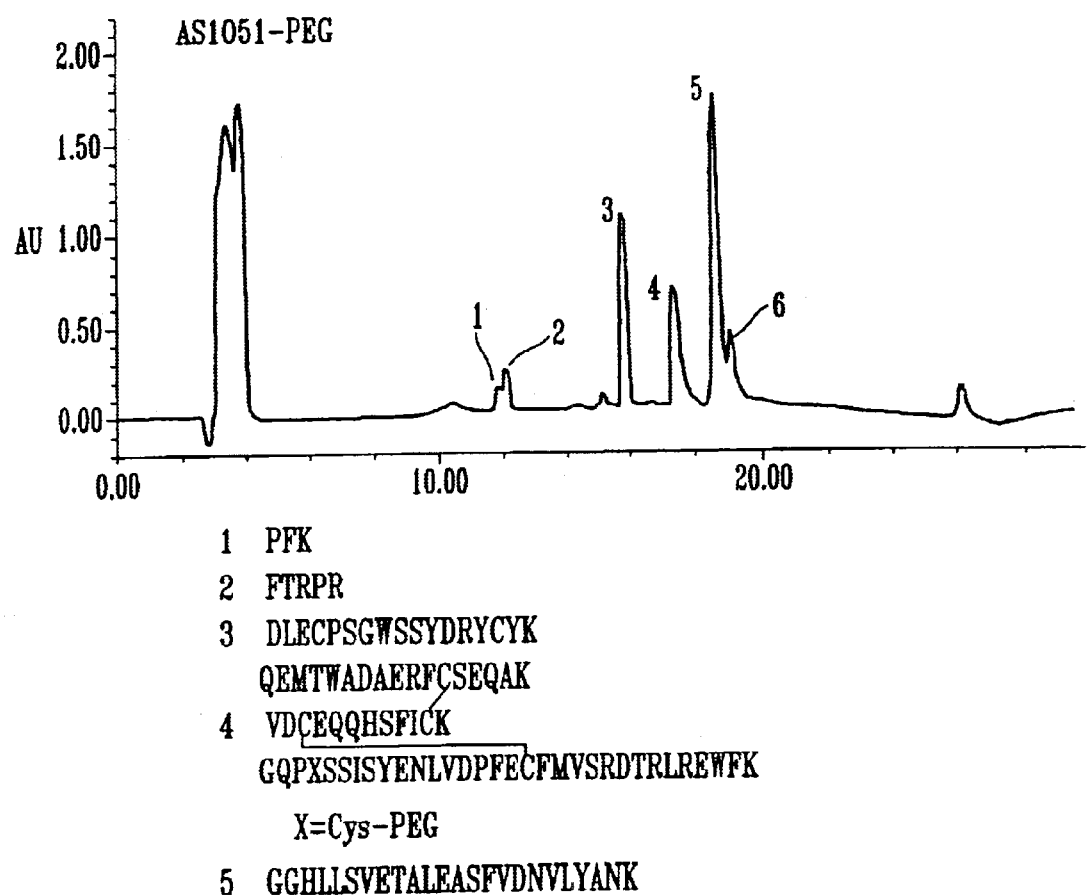

Subsequently, the polyethylene glycol-bonding position in AS1051-PEG5000 and linkage scheme of disulfide bonds in the other Cys residues were determined as follows. AS1051-PEG5000 (100 µg) was digested with lysyl endopeptidase (5 µg, Wako Pure Chemical Industries) in 0.1 M Tris-HCl buffer (pH 8.5) containing 2 mM EDTA at 37° C. for 5 hours and fractionated by high performance liquid chromatography using a reverse phase column (Vydac 218TP54, Vydac). Elution was performed with a linear gradient of water/acetonitrile containing 0.1% trifluoroacetic acid (TFA) (acetonitrile concentration of from 0 to 50% for 10 minutes, acetonitrile concentration of from 50% to 100% for 5 minutes). Thus, peptide chains obtained by digestion were obtained as Peaks 1 to 6 (FIG. 3). The amino acid sequence of each peptide chain was analyzed by using a protein sequencer Model 476A (Applied Biosystems). Since two Cys residues were contained in the chain of Peak 3, it was concluded that these two Cys residues were coupled to form a disulfide bond. Further, it was concluded that Peak 5 was composed of total three peptide chains, wherein two peptide chains containing one Cys residue and one peptide chain containing two Cys residues were coupled through disulfide bonds. The peptide chains of this Peak 5 were further digested with V8 protease (5 µg, Wako Pure Chemical Industries) in 10 mM ammonium carbonate buffer at 25° C. for 24 hours and fractionated by high performance liquid chromatography using a reverse phase column (Pegasil ODS-II, Senshu Kagaku). Elution was performed with a linear gradient of water/acetonitrile containing 0.1% TFA (acetonitrile concentration of from 0 to 50% for 20 minutes). Thus, peptide chains obtained by digestion were prepared and their amino acid sequences were analyzed. As a result, it was confirmed that the polyethylene glycol chain was bonded to a Cys residue corresponding to the amino acid number 81 in SEQ ID NO: 1 and all the peaks supported that the peptides of Peak 5 had such a disulfide bond as shown in FIG. 3. The bonding scheme of disulfide bond in AS1051-PEG determined as described above was the same as in the reported AS1051 (N. Fukuchi et al., WO95/08573) or other similar proteins originating from snake venom.

(3) Preparation of Polyethylene-glycolated Highly Active Protein

Subsequently, an expression gene for the M23-WT protein containing mutations of Asp54Asn and Asp101Ala as in the case of M23-G4 (corresponding to AS1051-WT protein containing two mutations of Asp54Asn and Asp101Ala) was prepared as follows. PCR was performed by using the expression plasmid pTrcASWT for AS1051 as a template, primers M16F (SEQ ID NO: 29) and M16R (SEQ ID NO: 30) and a QuickChange™ Site-Directed Mutagenesis Kit (Stratagene) to obtain an expression plasmid pTrcM16WT for a mutant protein M16-WT. Further, PCR was performed by using the expression plasmid pTrcM16WT as a template, primers M23F (SEQ ID NO: 43) and M23R (SEQ ID NO: 44) and the QuickChange™ Site-Directed Mutagenesis Kit (Stratagene) to obtain an expression plasmid pTrcM23WT for the mutant protein M23-WT. As in Example 6, the transformant E. coli JM109 strain harboring pTrcM23WT was cultured to obtain granules (inclusion bodies) as precipitates. The mutant protein M23-WT obtained as described above corresponded to the AS1051-WT protein containing two mutations of Asp54Asn and Asp101Ala.

Further, an expression gene for a mutant protein M23-Cys, in which one Gly residue closest to the amino terminus among the four Gly residues in M23-G4 was replaced with Cys for polyethylene-glycolation, was prepared as follows. PCR was performed by using the expression plasmid pTrcM23G4 for M23-G4 as a template, primers CGGGF (SEQ ID NO: 47) and CGGGR (SEQ ID NO: 48), and the QuickChange™ Site-Directed Mutagenesis Kit (Stratagene) to obtain an expression plasmid pTrcM23Cys for the mutant protein M23-Cys. As in Example 6, the transformant E. coli JM109 strain harboring pTrcM23Cys was cultured to obtain granules (inclusion bodies) as precipitates. The mutant protein M23-Cys obtained as described above corresponded to a protein in which the Gly residue closest to the amino terminus in the region of four continuous Gly residues of M23-G4 was mutated to Cys.

Subsequently, polyethylene-glycolation reaction was performed. First, granules obtained from 2 L of culture broth of the M23-WT were dissolved in 320 ml of 0.5 M Tris-HCl buffer (pH 8.5) containing 7 M guanidine hydrochloride and 10 mM EDTA. Then, distilled water was added in a volume of 2.5 times the solution and the mixture was left standing overnight at 4° C. Further, to this solution, 22.4 ml of 20 mg/ml aqueous solution of a polyethylene-glycolating reagent having a molecular weight of about 20,000 (Methoxy-PEG-mal, MW 20000, Item No.: M-MAL-20000, Shearwater Polymers) for binding to a thiol group of Cys was added and the mixture was allowed to react at 4° C. for about 2 hours. This solution was dialyzed against distilled water overnight at 4° C. by using a Spectra/Por 1 dialysis membrane (Spectra). To the obtained dialyzed solution (1.24 ml), 163.85 g of ammonium sulfate was added for salting out. The precipitates were removed by centrifugation and the supernatant was subjected to hydrophobic column chromatography using Butyl-Sepharose CL-4B FF (16×150 mm) (Pharmacia). The ammonium sulfate concentration of the elution solution was lowered from 1 M to 0 M (60 minutes) as a linear concentration gradient to collect a polyethylene-glycolated M23 (M23-PEG20000). Further, the collected fraction was dialyzed against distilled water by using a Spectra/Por 1 dialysis membrane (Spectra) to remove ammonium sulfate. To the fraction after the dialysis, 1/9 volume of 0.5 M ammonium acetate buffer (pH 4.5) was added, and the mixture was loaded on an ion exchange column using CM-TOYOPEARL 650S (2.6×40 cm) and eluted with Elution solution A (50 mM ammonium acetate buffer (pH 4.5)) and Elution solution B (0.5 M ammonium acetate buffer (pH 6.4)). The elution was performed with a mixed solution composed of Elution solutions A and B (A:B=80:20) for 20 minutes, and then with a linear gradient of from A:B=80:20 to A:B=55:45 for 30 minutes. Thus, an eluted fraction containing purified M23-PEG20000 was obtained. Further, the eluted fraction was concentrated by ultrafiltration and then purified by gel filtration using Sepharose CL-4B (26×900 mm) to finally obtain about 15 mg of M23-PEG20000. The protein concentration was quantified by comparing a peak area at 280 nm obtained in reverse phase HPLC with that of AS1051-Ala having a known concentration in the same manner as in Example 6.

Further, M23-PEG5000 bonded with polyethylene glycol having a molecular weight of about 5000 was prepared in the same manner as described above by using M-MAL-5000 (Methoxy-PEG-mal, MW5000, Shearwater Polymers) instead of M-MAL-20000. The obtained M23-PEG20000 and M23-PEG5000 showed bands at molecular weights of about 55 kDa and about 25 kDa, respectively, in SDS electrophoresis like AS1051-PEG2000 and AS1051-PEG5000.

Further, polyethylene-glycolation of M23-Cys was similarly performed by using the obtained granules.

Figure 4:
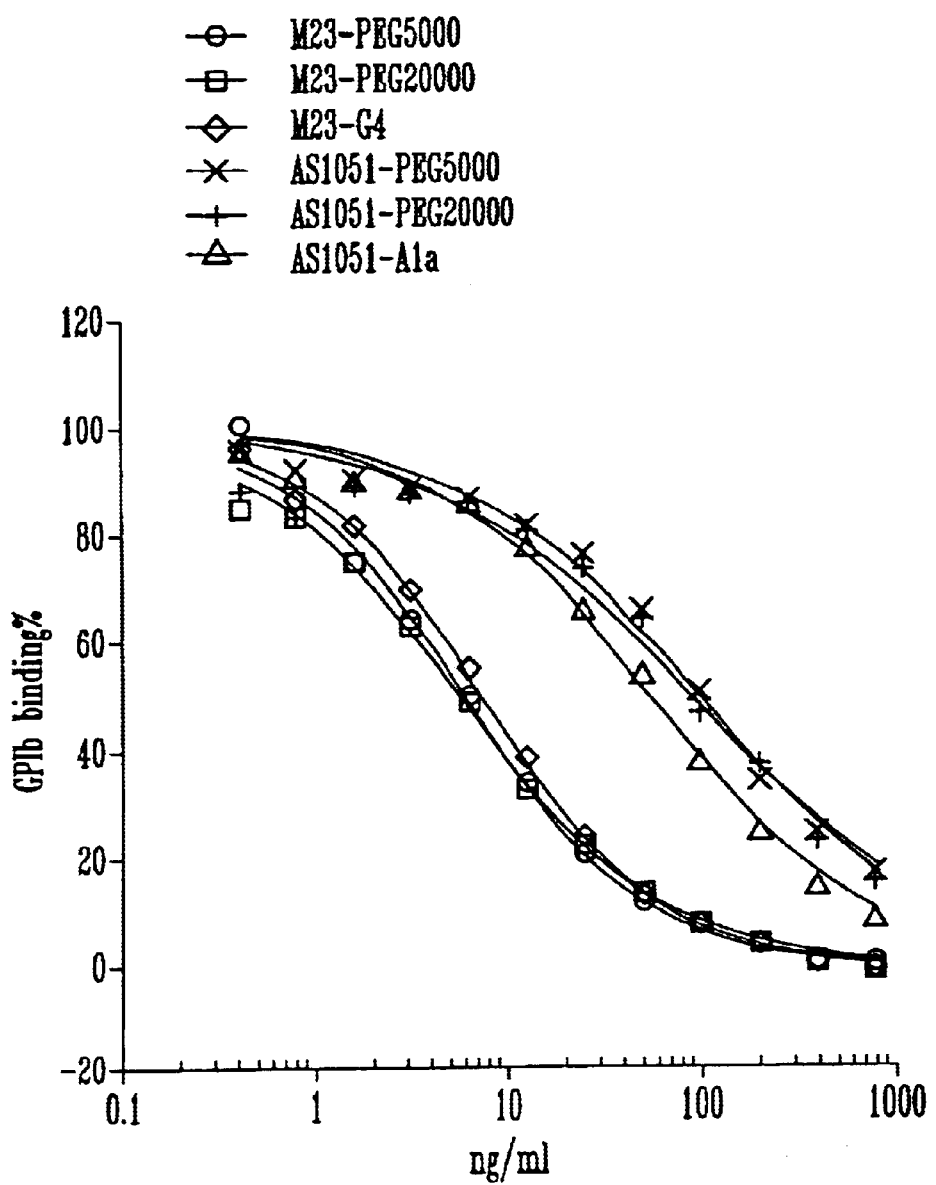
Figure 5A:
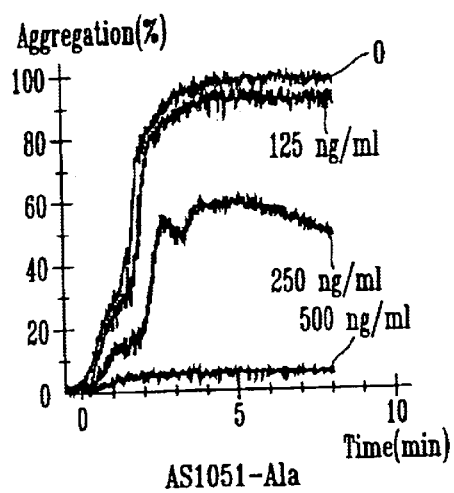
Figure 5B:
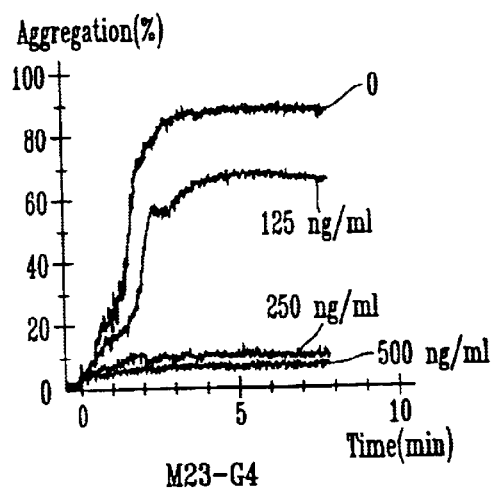
Figure 5C:
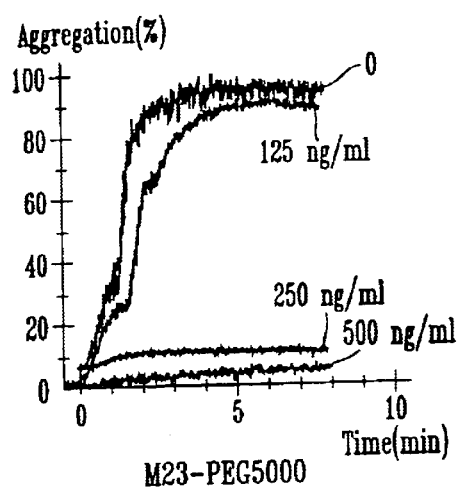
Figure 5D:
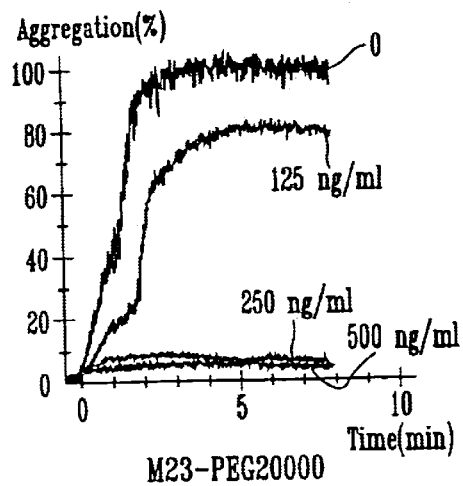

(4) Determination of Glycoprotein Ib/von Willebrand Factor Binding Inhibitory Activity of Polyethylene-glycolated Proteins By using the same method as in Example 5, the glycoprotein Ib/von Willebrand factor binding inhibitory activity of the prepared polyethylene-glycolated proteins M23-PEG5000 and M23-PEG20000 were compared with that of M23-G4 that was not polyethylene-glycolated, AS1051-Ala that was not mutated and polyethylene-glycolated AS1051. As shown in FIG. 4 and Table 5, all the proteins obtained by mutation of M23 exhibited the inhibitory activity about 10 times as strong as that of the others, and further increase of the inhibitory activity was obtained by polyethylene-glycolation.

TABLE 5

| Protein | $IC_{50}$ value (ng/ml) |
|---|---|
| AS1051-Ala | 54.4 |
| AS1051-PEG5000 | 98.1 |
| AS1051-PEG20000 | 90.3 |
| M23-G4 | 7.39 |
| M23-PEG5000 | 5.96 |
| M23-PEG20000 | 5.55 |

Further, the inhibitory activity of the above proteins for human platelet aggregation induced by ristocetin, ADP (adenosine diphosphate), collagen and low-concentration thrombin was determined. The human platelet rich plasma (PRP) was prepared as follows. Blood was collected from healthy volunteers by using an 18G injection needle. To the collected blood, 3.8% sodium citrate was added in 1/10 volume of the blood, and the mixture was centrifuged by a centrifugal machine under conditions of 900 rpm, 15 minutes and room temperature to collect the supernatant as PRP. The lower layer was further centrifuged under conditions of 1500 rpm, 10 minutes and room temperature to collect the supernatant as platelet poor plasma (PPP). Then, the platelet aggregation inhibitory activity of the above proteins was determined by using PRP prepared as described above and a Hematracer 801 (Niko Bioscience) as a measurement apparatus. To a special cuvette containing about 2.5 µl of a 20-fold solution of a protein to be determined, 100 µl of PRP was added, and the cuvette was set on the measurement apparatus, shaken for 2 minutes (37° C.). Then, a solution of an aggregation-inducing substance at 10-fold concentration, and changes in transmitted light were measured. The aggregation ratio was calculated on the assumption that the transmittance of read light before addition of the aggregation inducing substance was 0% and that the transmittance of PPP was 100%

As a result of the measurement, all the proteins exhibited no substantial inhibitory activity for aggregation induced by ADP and collagen, but a strong inhibitory activity for aggregation induced by ristocetin. The mutated M23 proteins exhibited stronger inhibitory activity. The aggregation curve of ristocetin-induced aggregation is shown in FIG. 5.

Figure 6A:
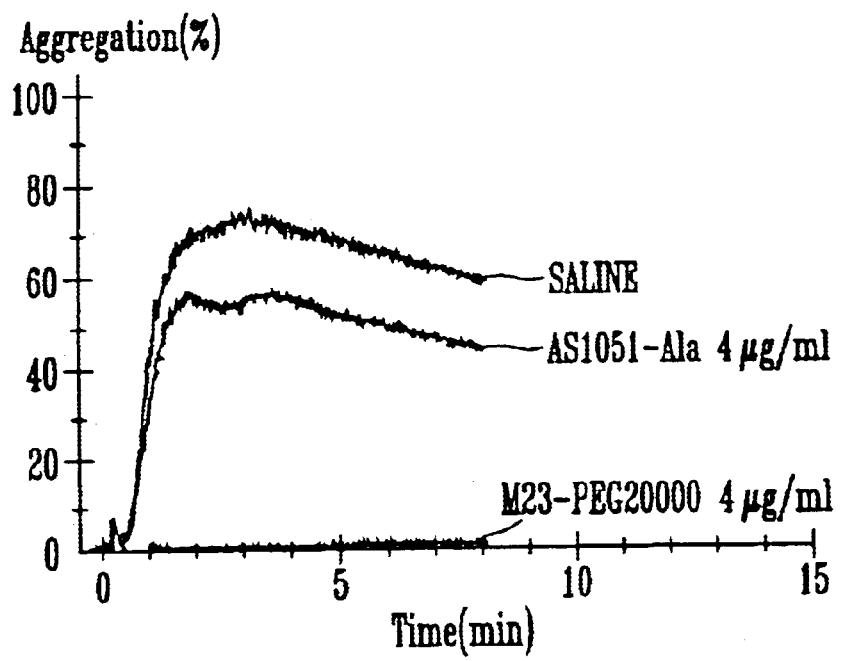
Figure 6B:
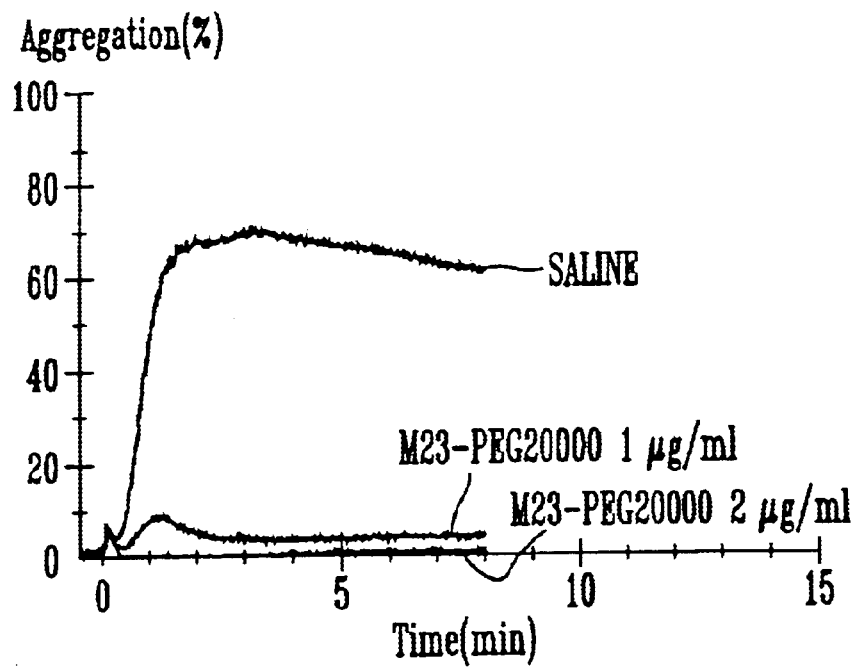

Further, the inhibitory activity for aggregation induced by low concentration thrombin was determined as follows. To 5 ml of PRP prepared in the same manner as described above, apyrase (grade VII, sigma) was added at a concentration of 8.3 U/ml and the mixture was incubated at 37° C. for 15 minutes. The reaction mixture was centrifuged at 2000 rpm for 10 minutes, and precipitated platelets were carefully suspended in a Tyrode-HEPES buffer containing apyrase (4.2 U/ml) and further centrifuged at 200 rpm for 10 minutes. Finally, precipitated platelets were suspended in a Tyrode-HEPES buffer containing 5 ml of 2 mM calcium chloride to obtain a washed platelet solution. Aggregation inhibition was measured by using the washed platelet solution instead of PRP and Tyrode-HEPES buffer instead of PPP by the same method as described above. The final concentration of thrombin was 0.07 U/ml. As a result, AS1051-Ala exhibited no substantial inhibition at a concentration of 4 µg/ml, whereas M23-PEG20000 almost completely inhibited thrombin-induced aggregation at a concentration of 1 µg/ml or higher (FIG. 6).

Example 8
Preparation of M23-Ala (Mutant M23 Protein that is not Shortened Protein (G4))

Further, a protein corresponding to M23-WT in which the Cys in position 81 in the amino acid sequence is mutated to Ala, M23-Ala, was prepared as follows. PCR was performed by using the expression plasmid pTrcM23WT for M23-WT as a template, primers ALAF-2 (SEQ ID NO: 49) and ALAR-2 (SEQ ID NO: 50) and a QuickChange™ Site-Directed Mutagenesis Kit (Stratagene) to obtain an expression plasmid pTrcM23Ala for M23-Ala. The transformant E. coli JM109 strain harboring the prepared expression plasmid pTrcM23Ala was cultured in L-broth (1% Bacto trypton, 0.5% yeast extract, 0.5% sodium chloride, 100 µg/ml ampicillin sodium) at 37° C. by using a Sakaguchi flask. IPTG (isopropyl-β-thiogalactopyranoside) was added at 10 mM when the turbidity reached 0.5 and further cultured at 37° C. for 4 hours. The microbial cells were collected and washed by centrifugation. Then, the microbial cells were suspended in 0.5 M EDTA solution. Lysozyme was added thereto and then left standing at room temperature for 1 hour. The suspension of the microbial cells was disrupted by an ultrasonicator (200 W, 5 minutes), and the disrupted suspension was centrifuged to obtain granules (inclusion bodies) as precipitates.

The obtained granules were dissolved in 0.5 M Tris-HCl buffer (pH 8.5) containing 7 M guanidine hydrochloride and 10 mM EDTA. Then, distilled water was added in a volume 2.5 times the solution and the mixture was left standing overnight at 4° C. The solution was dialyzed against 0.9% saline by using a Spectra/Por 1 dialysis membrane (Spectra) to remove guanidine hydrochloride. To the solution after the dialysis, 1/9 volume of 0.5 M ammonium acetate buffer (pH 4.5) was added, and the mixture was loaded on an ion exchange column using CM-TOYOPEARL 650S (2.6×40 cm) and eluted with Elution solution A (50 mM ammonium acetate buffer (pH 4.5)) and Elution solution B (0.5 M ammonium acetate buffer (pH 6.4)). The elution was performed with a solution composed of Elution solutions A and B (A:B=30:70) for 20 minutes, and then with a linear gradient of from A:B=30:70 to A:B=0:100 for 30 minutes. Thus, an eluted fraction containing purified M23-Ala was obtained. The protein was quantified by comparing elution peak areas at 280 nm obtained by reverse phase HPLC using Pegasil ODS-300 (4.6×250 mm, Senshu Kagaku) by using AS1051-Ala (see Example 1) and AS1051-G4 (see Example 2) quantified beforehand using a Bio-Rad Protein Assay (Bio-Rad) as standards. When the glycoprotein Ib/von Willebrand factor binding inhibitory activity of M23-Ala was determined in the same manner as in Examples 5 and 6, the inhibitory activity was almost comparable to that of M23.

Example 9
Antigenicity Test of AS1051-Ala in Guinea Pig

Figure 7:
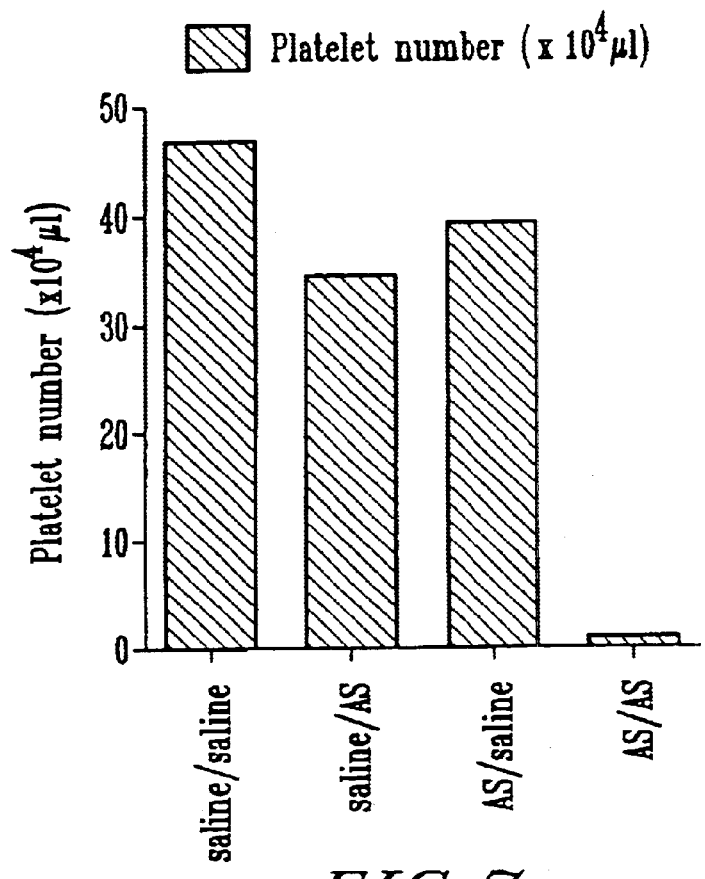

To Confirm antigenicity in a guinea pig of the AS1051 protein in which cysteine residue in position 81 was replaced with an Ala residue (AS1051-Ala), which was prepared as shown in Example 1, a test was performed as follows. Two groups of female Hartley guinea pigs (body weight 200 to 250 g) were administered with AS1051-Ala (300 µg/kg) or physiological saline from auricular veins three times every other day. The dose was 1 ml/kg and each group was composed of 10 animals (n=10). Following 3 weeks after the third administration, each administration group was further divided into two groups, each of which was administered with AS1051-Ala (300 µg/kg) (n=5 each) or physiological saline (n=5 each). About 20 minutes later, abdominal section was performed under etherization and 8 ml of blood was collected from the abdominal aorta (0.38% sodium citrate was added) by using a 23G injection needle. The number of platelets in the collected blood was measured by using an automatic cell counter (Sysmex E-2000, Toa Medical Electronics). The results are shown in FIG. 7. A marked decrease of platelets was observed only in the group in which AS1051-Ala was administered at preliminary and final administrations (AS/AS group). In the group in which physiological saline was administered at preliminary administration and AS1051-Ala was administered at final administration (saline/AS group), the number of platelets was substantially the same as that of the saline/saline group as a control group. Therefore, it was considered that the decrease of platelets observed in the AS/AS group was attributable to the antigenicity of AS1051-Ala administered at preliminary administration.

Figure 8:
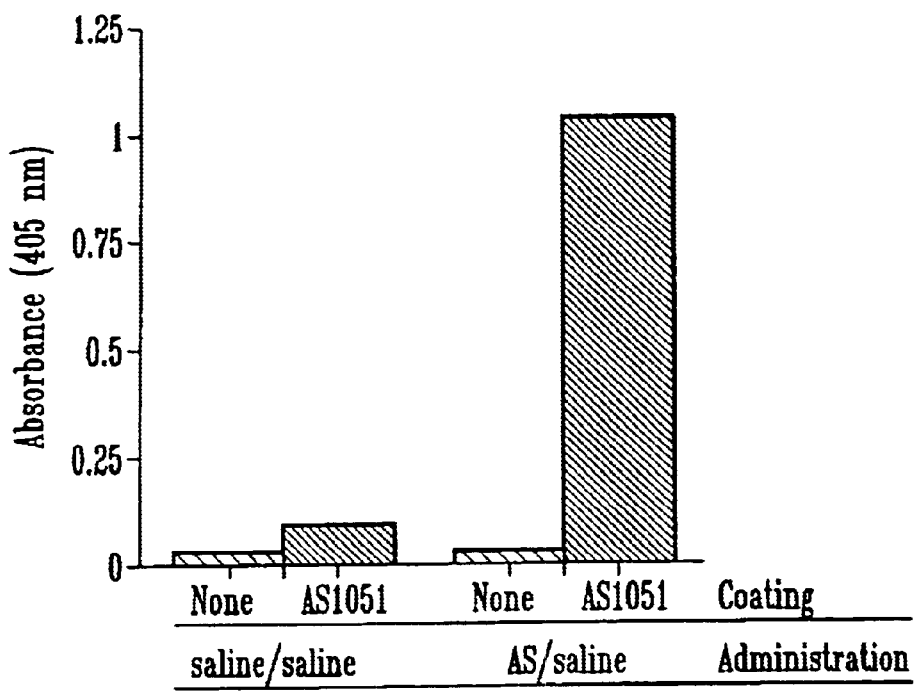

Further, plasma was separated from the collected blood by centrifugation (4° C., 2700 rpm, 10 minutes), and the presence of antibodies to AS1051-Ala was determined by the enzyme-linked immunosorbent assay (ELISA) method. 50 µl of AS1051-Ala (1 µg/ml) or only a buffer was added to each well of a 96-well plate for ELISA and left standing overnight at 4° C. to coat the well. Then, each well was washed three times with phosphate-buffered saline (PBS) containing 0.05% Tween-20 and blocked with PBS (150 µl) dissolving 5% skim milk. Each well was further washed three times. Then, 50 µl of the collected guinea pig plasma was added thereto and the plate was left at 37° C. for 1 hour. Then, each well was washed three times. 50 µl of a solution obtained by diluting alkaline phosphatase-labeled rabbit anti-guinea pig IgG (H+L) antibodies (Zymed) 500-fold with a dilution buffer (0.05 M Tris-HCl (pH 8.1), 1 mM $MgCl_2$, 0.15 M NaCl, 0.05% Tween-20, 0.02% $NaN_3$, 1% bovine serum albumin) was added thereto and the plate was left at 37° C. for 1 hour. Each well was washed three times and 1 mg/ml of chromogenic substrate (p-nitrophenylphosphate) solution (1 M diethanolamine (pH 9.8)/0.5 mM $MgCl_2$) was added. After an appropriate time for the reaction, absorption was measured at 405 nm. FIG. 8 shows absorption of reaction mixtures in the wells coated with AS1051-Ala and the wells without coating for the AS/saline group and the saline/saline group. As shown in the figure, the presence of antibodies bound to AS1051-Ala was demonstrated in the AS/saline group.

Example 10
Antigenicity Test of AS1051-G4 in Guinea Pig

Figure 9:
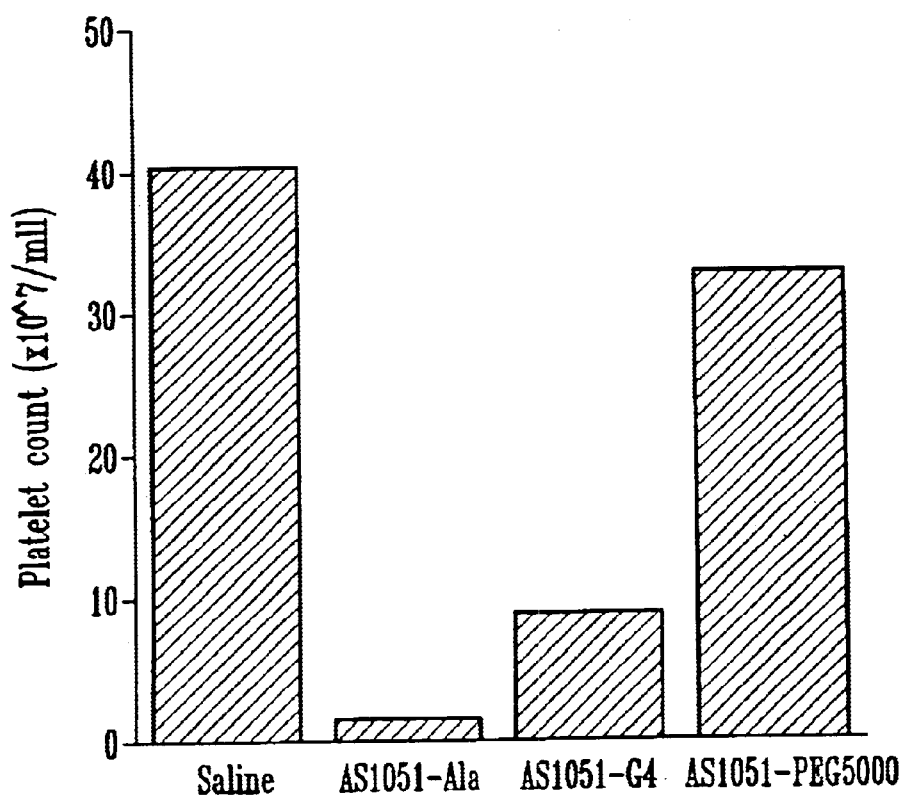
Figure 10A:
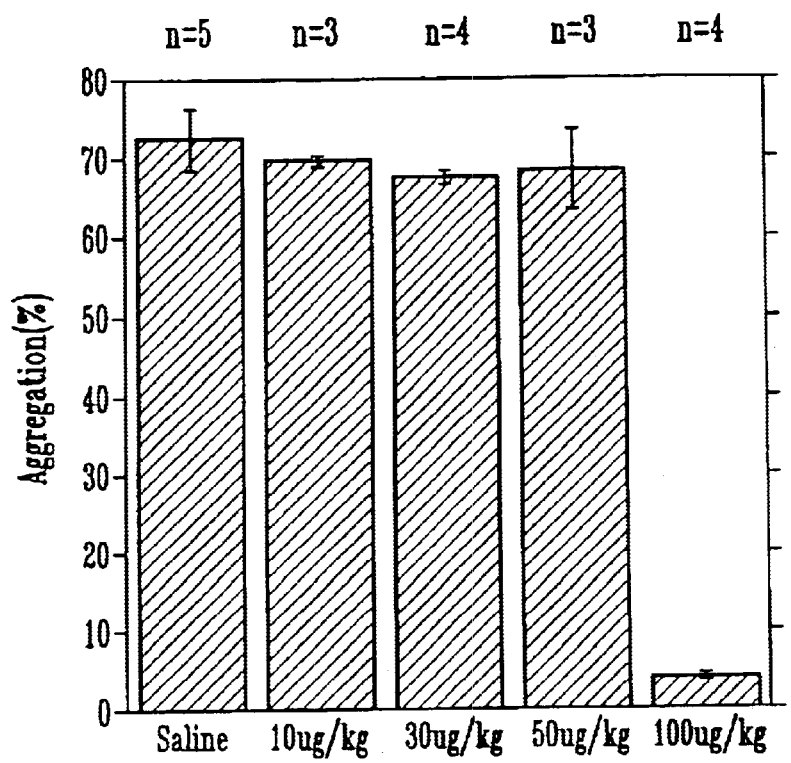
Figure 10B:
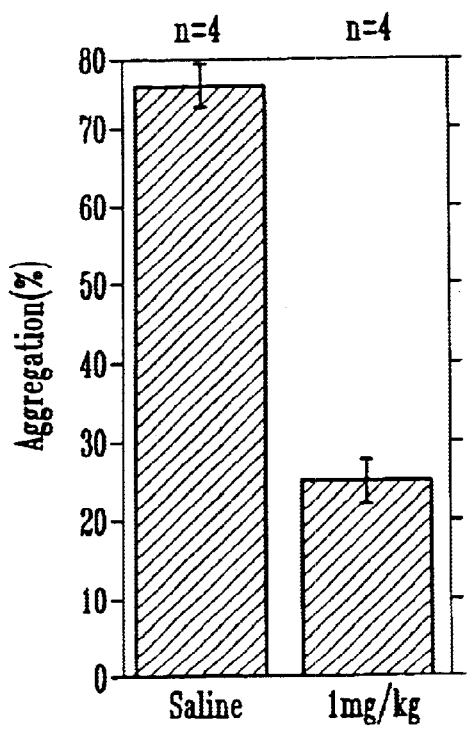

A test in a guinea pig for comparing antigenicity of the loop structure-deleted protein (AS1051-G4) and polyethylene-glycolated protein (AS1051-PEG5000) according to the present invention and AS1051-Ala was performed in the same manner as in the method described in Example 9. The doses of AS1051-Ala and AS1051-G4 were 200 µg/kg for any administration. The subjects were divided into four groups of the AS1051-Ala group (three times of preliminary administration of AS1051-Ala and final administration of AS1051-Ala), AS1051-G4 group (three times of preliminary administration of AS1051-G4 and final administration of AS1051-G4), AS1051-PEG5000 group (three times of preliminary administration of AS1051-PEG5000 and final administration of AS1051-PEG5000) and saline group (three times of preliminary administration of physiological saline and final administration of physiological saline), each being composed of 4 animals, to perform an experiment. As a result, as shown in FIG. 9, both of the AS1051-G4 group and the AS1051-PEG5000 group exhibited weaker platelet decrease action compared with that of the AS1051-Ala group.

Example 11
Ex vivo Drug Efficacy Test of Polyethylene-glycolated Highly Active Protein An ex vivo drug efficacy test of M23-PEG20000 in guinea pig was performed as follows. First, M23-PEG20000 physiological saline solutions were prepared at various concentrations, and female Hartley guinea pigs (body weight 350 to 400 g) were administered with 1 ml/kg of M23-PEG20000 solution at each concentration or physiological saline as a control group from auricular veins. Five minutes or 5 days (120 hours) after the administration, abdominal section was performed under etherization and blood was collected from the abdominal aorta (0.38% sodium citrate was added) by using a 23G injection needle. The number of platelets in the collected blood was measured by using an automatic cell counter (Sysmex E-2000, Toa Medical Electronics). Further, the collected blood was centrifuged under conditions of 1100 rpm, 15 minutes and room temperature to prepare PRP. Further, the lower layer was centrifuged under conditions of 2700 rpm, 15 minutes and room temperature to prepare PPP. To the obtained PRP, botrocetin was added as a platelet aggregation inducing substance, and the maximum botrocetin-induced aggregation rate in 8 minutes was measured for each group by using the same platelet aggregometer as used in the method of Example 7. As a result, among the groups in which blood was collected 5 minutes after the administration of M23-PEG20000, the 100 μg/kg administered group exhibited a significant inhibitory effect on aggregation as shown in FIG. 10(*a*). Further, the 1 mg/kg administered group exhibited strong inhibition on botrocetin-induced aggregation even in the blood collected 5 days (120 hours) after the administration (FIG. 10(*b*)). Thus, it was confirmed that the inhibitory effect on glycoprotein Ib/von Willebrand factor binding was maintained even for 5 days (120 hours) after the administration at that dose. Further, no significant change in the number of blood cells was observed in all of the groups.

What is claimed is:

1. A protein comprising an amino acid sequence with a homology of not less than 30% to the amino acid sequence of SEQ ID NO: 1 and forms a secondary or tertiary structure composed of a first β strand (β1), a first α helix (α1), a second α helix (α2), a second β strand (β2), a loop, a third β strand (β3), a fourth β strand (β4) and a fifth β strand (β5) in this order from the amino terminus, and wherein at least one amino acid residue in a region from α2 to β2, a region from β3 to β4, or in the regions from α2 to β2 and from β3 to β4 is replaced so that electric charge of the amino acid residue is changed towards positive direction as compared to the unsubstituted amino acid, said protein being the following (a) or (b):
   (a) a protein, in which the region from α2 to β2 has the sequence of the amino acid residues 47 to 72 in the amino acid sequence of SEQ ID NO: 1 and the region from β3 to β4 has the sequence of the amino acid residues 94 to 111 in the amino acid sequence of SEQ ID NO: 1;
   (b) the protein according to (a), in which substitution, insertion or deletion of one amino acid residue is included in the region from α2 to β2 having the sequence of the amino acid residues 47 to 72 in the amino acid sequence of SEQ ID NO: 1, or the region from β3 to β4 having the sequence of the amino acid residues 94 to 111 in the amino acid sequence of SEQ ID NO: 1; and
   wherein said protein has antithrombotic activity.

2. The protein according to claim 1, wherein the protein is bonded to a polyoxyalkylpolyol group via a reactive functional group wherein said reactive functional group is selected from the group consisting of an amino reactive functional group, a carboxyl reactive functional group, and a thiol reactive functional group.

3. The protein according to claim 1, wherein the protein is bonded to a polyoxyalkylpolyol group via a thiol reactive functional group.

4. The protein according to claim 3, wherein said thiol reactive functional group is selected from the group consisting of a maleimide group, an orthopyridyl disulfide group, and a vinylsulfone group.

5. A protein comprising an amino acid sequence with a homology of not less than 30% to the amino acid sequence of SEQ ID NO: 1 and forms a secondary or tertiary structure composed of a first β strand (β1), a first α helix (α1), a second α helix (α2), a second β strand (β2), a loop, a third β strand (β3), a fourth β strand (β4) and a fifth β strand (β5) in this order from the amino terminus, and wherein at least one amino acid residue in a region from α2 to β2, a region from β3 to β4, or in the regions from α2 to β2 and from β3 to β4 is substituted so that electric charge of the amino acid residue is changed towards positive direction as compared to the unsubstituted amino acid, said protein being the following (a) or (b):
   (a) a protein, in which the region from α2 to β2 has the sequence of the amino acid residues 47 to 72 in the amino acid sequence of SEQ ID NO: 1 and the region from β3 to β4 has the sequence of the amino acid residues 94 to 111 in the amino acid sequence of SEQ ID NO: 1;
   (b) the protein according to (a), in which substitution, insertion or deletion of one amino acid residue is included in the region from α2 to β2 having the sequence of the amino acid residues 47 to 72 in the amino acid sequence of SEQ ID NO: 1, or the region from β3 to β4 having the sequence of the amino acid residues 94 to 111 in the amino acid sequence of SEQ ID NO: 1; and
   wherein said protein has antithrombotic activity,
   and wherein said protein comprises an amino acid sequence of the following (A) or (B):
   (A) the amino acid sequence of the amino acid residues 47 to 111 in the amino acid sequence of SEQ ID NO: 1;
   (B) the amino acid sequence according to (A), in which the cysteine residue of the amino acid residue 81 in the amino acid sequence of SEQ ID NO: 1 is replaced with an alanine residue.

6. A protein comprising an amino acid sequence with a homology of not less than 30% to the amino acid sequence of SEQ ID NO: 1 and forms a secondary or tertiary structure composed of a first β strand (β1), a first α helix (α1), a second α helix (α2), a second β strand (β2), a loop, a third β strand (β3), a fourth β strand (β4) and a fifth β strand (β5) in this order from the amino terminus, and wherein at least one amino acid residue in a region from α2 to β2, a region from β3 to β4, or in the regions from α2 to β2 and from β3 to β4 is substituted so that electric charge of the amino acid residue is changed towards positive direction as compared to the unsubstituted amino acid, said protein being the following (a) or (b):

(a) a protein, in which the region from α2 to β2 has the sequence of the amino acid residues 47 to 72 in the amino acid sequence of SEQ ID NO: 1 and the region from β3 to β4 has the sequence of the amino acid residues 94 to 111 in the amino acid sequence of SEQ ID NO: 1;

(b) the protein according to (a), in which substitution, insertion or deletion of one amino acid residue is included in the region from α2 to β2 having the sequence of the amino acid residues 47 to 72 in the amino acid sequence of SEQ ID NO: 1, or the region from β3 to β4 having the sequence of the amino acid residues 94 to 111 in the amino acid sequence of SEQ ID NO: 1; and wherein said protein has antithrombotic activity, and wherein said protein has the amino acid sequence in which a region containing the loop structure existing between β2 and β3 is deleted in such a manner that the secondary or tertiary structures of β2 and β3 are maintained, or the region is replaced with one or more amino acid residue(s) in a number required to maintain the secondary or tertiary structures of β2 and β3, said amino acid residue(s) being selected from the group consisting of a glycine residue, an alanine residue, a serine residue and a cysteine residue.

7. The protein according to claim 6, wherein the region containing the loop structure existing between β2 and β3 is replaced with an amino acid sequence composed of four glycine residues.

8. A protein comprising an amino acid sequence with a homology of not less than 30% to the amino acid sequence of SEQ ID NO: 1 and forms a secondary or tertiary structure composed of a first β strand (β1), a first α helix (α1), a second α helix (α2), a second β strand (β2), a loop, a third β strand (β3), a fourth β strand (β4) and a fifth β strand (β5) in this order from the amino terminus, and wherein at least one amino acid residue in a region from α2 to β2, a region from β3 to β4, or in the regions from α2 to β2 and from β3 to β4 is substituted so that electric charge of the amino acid residue is changed towards positive direction as compared to the unsubstituted amino acid, said protein being the following (a) or (b):

(a) a protein, in which the region from α2 to β2 has the sequence of the amino acid residues 47 to 72 in the amino acid sequence of SEQ ID NO: 1 and the region from β3 to β4 has the sequence of the amino acid residues 94 to 111 in the amino acid sequence of SEQ ID NO: 1;

(b) the protein according to (a), in which substitution, insertion or deletion of one amino acid residue is included in the region from α2 to β2 having the sequence of the amino acid residues 47 to 72 in the amino acid sequence of SEQ ID NO: 1, the region from β3 to β4 having the sequence of the amino acid residues 94 to 111 in the amino acid sequence of SEQ ID NO: 1 and wherein said protein has antithrombotic activity, and wherein at least one acidic amino acid residue of which α carbon atom exists within 10 Å from the α carbon atom of the arginine residue of the amino acid number 103 in the amino acid sequence of SEQ ID NO: 1 is replaced with a neutral amino acid residue.

9. The protein according to claim 8, wherein the acidic amino acid residue to be replaced is composed of at least one residue selected from the aspartic acid residue of the amino acid residue 54, the aspartic acid of the amino acid residue 101 and the glutamic acid residue of the amino acid residue 106 in the amino acid sequence of SEQ ID NO: 1.

10. The protein according to claim 1, wherein the protein is bonded to a polyoxyalkylpolyol group.

11. The protein according to claim 10, wherein the protein contains a cysteine residue corresponding to a cysteine residue of the amino acid residue 81 in the amino acid sequence of SEQ ID NO: 1 and the polyoxyalkylpolyol group is bonded to said cysteine residue.

12. The protein according to claim 10, wherein the polyoxyalkylpolyol group is a polyethylene glycol group.

13. A drug comprising the protein as claimed in claim 1 as an active ingredient.

14. A drug comprising the protein as claimed in claim 5 as an active ingredient.

15. A drug comprising the protein as claimed in claim 6 as an active ingredient.

16. A drug comprising the protein as claimed in claim 7 as an active ingredient.

17. A drug comprising the protein as claimed in claim 8 as an active ingredient.

18. A drug comprising the protein as claimed in claim 9 as an active ingredient.

19. A drug comprising the protein as claimed in claim 10 as an active ingredient.

\* \* \* \* \*